US010286254B2

(12) United States Patent
French

(10) Patent No.: US 10,286,254 B2
(45) Date of Patent: May 14, 2019

(54) ASSESSMENT AND ENHANCEMENT OF REACTION BASED JOINT STABILIZATION CAPABILITIES

(71) Applicant: Barry James French, Bay Village, OH (US)

(72) Inventor: Barry James French, Bay Village, OH (US)

(*) Notice: Subject to any disclaimer, the term of this patent is extended or adjusted under 35 U.S.C. 154(b) by 0 days.

(21) Appl. No.: 15/960,992

(22) Filed: Apr. 24, 2018

(65) Prior Publication Data

US 2018/0304118 A1    Oct. 25, 2018

Related U.S. Application Data

(60) Provisional application No. 62/707,464, filed on Nov. 4, 2017, provisional application No. 62/605,473, filed
(Continued)

(51) Int. Cl.
| *A63B 24/00* | (2006.01) |
| *A61B 5/11* | (2006.01) |
| *G09B 9/00* | (2006.01) |
| *A61B 5/00* | (2006.01) |
| A63B 69/00 | (2006.01) |
| A63B 69/34 | (2006.01) |
| A63B 71/00 | (2006.01) |
| A63B 22/00 | (2006.01) |

(52) U.S. Cl.
CPC ........ *A63B 24/0006* (2013.01); *A61B 5/1124* (2013.01); *A61B 5/4519* (2013.01); *A61B 5/7275* (2013.01); *G09B 9/00* (2013.01); *A61B 5/1127* (2013.01); *A61B 5/6801* (2013.01); *A61B 5/744* (2013.01); *A61B 2503/10* (2013.01); *A61B 2505/09* (2013.01); *A63B 69/0053* (2013.01); *A63B 69/34* (2013.01); *A63B 71/0054* (2013.01); *A63B 2022/0092* (2013.01); *A63B 2024/0015* (2013.01); *A63B 2220/05* (2013.01); *A63B 2220/13* (2013.01); *A63B 2220/806* (2013.01)

(58) Field of Classification Search
CPC . A61B 5/4528; A61B 5/11; A63B 2024/0015; A63B 24/0006
See application file for complete search history.

(56) References Cited

U.S. PATENT DOCUMENTS

| 4,971,069 A * | 11/1990 | Gracovetsky ........ A61B 5/0488 600/594 |
| 2014/0107429 A1 * | 4/2014 | Simkovich ............... A61B 5/16 600/300 |
| 2014/0142439 A1 * | 5/2014 | French ................. A61B 5/4088 600/483 |

* cited by examiner

*Primary Examiner* — Jerry-Daryl Fletcher

(57) ABSTRACT

Interactive system provides training and assessments relating to joint stabilization capabilities and reaction-based performance for diverse populations. This system may enhance the subject's ability to generate and deliver power as a direct byproduct of properly timed decelerations originating with the effectors and supported by the verticality of the spine. Said decelerations also provide functional means for improving joint stabilization capabilities via improved co-contraction of the shoulder(s) joints and other anatomical locations on the subject. The resulting data may serve as the basis for predictive analytics relating to joint stabilization and the associated risk of orthopedic injuries. This system may also train/improve the dampening of internal forces resulting from aggressive weight bearing movements, and more effectively dissipate the force of received physical impacts.

19 Claims, 8 Drawing Sheets

Related U.S. Application Data on Aug. 14, 2017, provisional application No. 62/604,141, filed on Jun. 23, 2017, provisional application No. 62/508,067, filed on May 18, 2017, provisional application No. 62/489,689, filed on Apr. 25, 2017.

ASSESSMENT AND ENHANCEMENT OF REACTION BASED JOINT STABILIZATION CAPABILITIES

RELATED APPLICATIONS

This application claims priority to U.S. Provisional Application No. 62/489,689, filed Apr. 25, 2017, which claims priority under 35 USC 119 to U.S. Provisional Application No. 62/508,067, filed May 18, 2017. This application also claims priority under U.S. Provisional Application No. 62/604,141, filed Jun. 23, 2017, and to US Provisional Application No. 62/605,473, filed Aug. 14, 2017, and to US Provisional Application No. 62/707,464 filed Nov. 4, 2017. All of the forgoing applications are incorporated by reference herein in their entireties.

FIELD OF THE INVENTION

The present invention is in the field of the assessment and enhancement of reaction-based joint stabilization and related performance capabilities.

DESCRIPTION OF THE RELATED ART

The American Academy of Orthopedic Surgeons estimated that 126.6 million Americans (one in two adults) are affected by a musculoskeletal condition. Annual cost is estimated at $213 billion in treatment, care and lost wages, according to a new report. Musculoskeletal disorders, defined as conditions and injuries affecting the bones, joints and muscles, can be painful and debilitating, affecting daily quality of life, activity and productivity.

There's a widely recognized need for improved methods to prevent and rehabilitate orthopedic injuries, specifically joint injuries, for populations ranging from youth/scholastic to professional athletes, the military, as well as senior populations. However, the literature suggests that present approaches for the treatment of musculoskeletal injuries are inadequate to restore neuromuscular control to a proficiency that reduces the risk of re-injury so as to minimize future risk of re-injury or continuing dysfunction.

Identified approaches for testing and reduction of the risk of musculoskeletal injury are not promoted in the literature; nor are means of detecting subtle defects of the integration of a subject's visual-cognitive-motor systems.

The literature suggests that the value of tests and training modalities may improve when they place the subject under visual and cognitive stress while concurrently eliciting from the subject the expeditious completion of a complex motor activation pattern.

Known methods to improve joint function and/or stabilization focus on joint range of motion, strength and coordination. Such methods are apparently delivered in a fashion that does not simulate/replicate real world reaction-based activities. By way of example, these real-world activities may include: a football tackle or block, defending the goal in soccer, throwing a punch while boxing, safely navigating one's environment, performing tasks of daily living, etc. In each of the aforementioned examples, reaction-based movements may expose the subject to a higher risk of joint injury.

The aforementioned brief overview of relevant science is believed to suggest that simultaneously challenging a subject's sensory, cognitive and neuromuscular systems is important for programs designed for the prevention of orthopedic/joint injuries, as well as enhancing reaction-based performance.

Joint Stabilization

The following section summarizes certain current research regarding the coordination of a subject's sensory, cognitive and neuromuscular systems, and how these systems may function together during complex, reaction-based movement to improve joint stabilization/safety and reaction-based performance. It is believed such observations may provide support for the present invention.

Identified current methods focused on programs to improve joint stability, safety and reaction-based performance are relegated to improving isolated capacities, i.e.: strength, range of motion, arm speed and similar. By contrast, the present invention integrates whole body sensory, cognitive, neuromuscular and musculoskeletal components to engage the involved joint(s) synergistically and holistically to perform with the body in its entirety. And perhaps most importantly, impose on the subject movement demands that accurately mimic real-world challenges.

Literature suggests that joint stabilization benefits from effective co-contractions that act to modulate the forces generated by the involved muscle groups, all of which benefit from the brain's programming. This may be especially beneficial for athletes seeking to prevent joint injuries, or to improve reaction times and motor skills.

For a joint, such as the shoulder, for example, the contraction of the agonist and co-contraction of the antagonist muscle groups increases joint stiffness, accordingly, the properly timed activation of the involved muscles is likely to increase joint stability.

Altered dynamic muscle contraction around the shoulder complex is assumed to be a material factor to shoulder dysfunction. In fact, muscle force associated with the shoulder complex may be more important than muscle strength for normal joint function.

Additionally, proprioception provides important feedback for the synergistic contraction of muscle groups and therefore may be vital both for normal functioning of the muscle groups of the shoulder joint and in protecting the shoulder against potential instability.

The present invention introduces reaction based, real world tasks that are believed to rely on increasing levels of "muscle force" rather than muscle strength, thereby facilitating "a synergistic contraction of relevant muscle groups."

Taught herein is the use of simulation to teach the principles of the present invention and the proper "lock down" of one's shoulder during the execution of a punch, etcetera. "Locking down" is the term used in certain martial arts to describe "a synergistic contraction of relevant muscle groups."

In response to a spontaneous visual stimulus, the forceful deceleration of the hand (the "effector" in this example) acts to impose a realistic, internally generated stress on the involved joints; for example, the involved shoulder, to improve joint stabilization and reaction-based performance in a novel fashion.

The present invention's purpose is to advance current practices in the fields of geriatrics, orthopedics, performance enhancement, neurology and physical rehabilitation. Currently, said practices may fail to deliver efficacious assessments and programming that deliver full body, reaction-based protocols to improve joint stabilization capacities and reaction-based performance for all weight bearing populations.

Training and testing methods that concurrently deliver a combination of complex sensory, cognitive, neuromuscular and musculoskeletal challenges are believed most capable of detecting and training those at risk for musculoskeletal injury.

Maintaining joint stability and preventing injury rely on the nervous system to effect changes to joint mechanics. Both the mechanical and neurological aspects of a joint must synergistically prepare for potentially threatening perturbations. Optimal muscle tone may optimize joint stiffness as so needed.

Studies have found that volitional muscle activity has a material effect on joint stiffness. The ability to anticipate the need for increased muscle stiffness is important for dynamic stabilization of involved body segments.

Post-injury return to normal activity is typically based on relatively arbitrary/subjective standards for adequate resolution of acute impairments (e.g., pain, swelling, motion restriction, weakness, etc.). Consequently, many patients return to physically demanding activities without having fully regained the ability to generate effective muscle responses to rapidly changing environmental conditions.

Furthermore, the utility of assessments and training activities may increase when they challenge a subject's capability to rapidly plan and execute a complex motor activation pattern under cognitive or visual stress.

Improvement of both neuromechanical coupling and full body joint stabilization capabilities is believed requisite to projecting power as well as protecting involved joints such as the shoulder, knee, elbow and neck.

In summary, elucidated from the research discussed above, the objectives for the present invention's novel capabilities include:

Testing procedures that combine visual-proprioceptive-cognitive-motor capabilities to identify individuals who possess suboptimal neuromechanical performance, as well as reaction-based performance capabilities.

Integration of visual-cognitive-motor training methods resulting in more optimal neuromechanical performance capabilities, as well as the imposition of simultaneous visual-proprioceptive-cognitive-motor demands to produce favorable adaptations beyond those achieved by isolated training.

Demonstration of the relevance of neuromechanical responsiveness to the capabilities of weight bearing populations to perform role-specific functions in an optimal manner.

SUMMARY OF THE INVENTION

The following features, described in terms of aspects and embodiments of the invention, may be combined in any combination into a single method/system.

According to an embodiment of any paragraph(s) of this summary, simulations train the subject's (athlete, soldier, senior, etcetera) sensory, cognitive, neuromuscular and musculoskeletal systems in a realistic manner. The subject thus learns to more adeptly deal with received physical impacts, to generate and deliver power as a direct byproduct of precisely timed decelerations of correctly aligned body segments, and to more efficiently resolve (dissipate) the internal forces generated during aggressive reaction-based movements.

According to an aspect of the invention, the objective is to materially reduce joint injuries (knee, shoulder, elbow etcetera) and concussions (brain injuries) while enhancing reaction-based performance, especially for populations suffering such injuries in alarming numbers such as female athletes, football players, the military, the aging, etcetera.

According to another aspect of the present invention, performance and kinematic data that is related to the risk of joint and brain injury may contribute to return to play (rehab) assessments as well as sport specific performance enhancement and injury prevention programming.

Aspects of the present invention may involve sport simulations to replicate the dynamic environment of sport. By way of example, there is a widely recognized need for improved methods of the teaching and training of football tackling, blocking and block destruction techniques without the inherent risks of physical contact, from youth/scholastic athletes to the NFL.

According to an embodiment of any paragraph(s) of this summary, as will be explained further, the emphasis Is on the initiating acceleration, for example, of the arm/hand, and on the timing and magnitude of the subsequent terminating deceleration of said arm/hand at the instant of a virtual tackle, block, block destruction, or other "physical" encounter.

An aspect of the present invention teaches the concept of the Deceleration Constellation ("DC"), which is defined herein as the moment to moment spatial and temporal relationship of a cluster ("an array") of anatomical points tracked on a person during interactive testing, training and rehabilitation simulations.

The present disclosure teaches protocols taught herein relating to the "purposeful" deceleration of the involved hands (or other "effectors") when interacting with a visually presented target/challenge in (virtual) space. The objective is to forcefully "brake" on virtual "contact" rather than accelerate through the virtual target, thereby consistent with the principles of the present invention.

According to an embodiment of any paragraph(s) of this summary, the magnitude of the real-world subject's deceleration associated with the execution of a technique is assessed either: 1). prior (close) to an actual (virtual) impact of the target, or 2). upon virtual contact.

According to another aspect of the invention, by way of example, at the instant of (virtual) contact, the subject decisively contracts/activates the relevant muscle groups, i.e. braking/antagonistic muscles, while adhering to proper (blocking, for example) form to practice the present disclosure.

Aspects of the present invention teach correct form (technique) during the execution of a properly timed and correctly executed response, such as with a simulated tackle, block, punch, catch, throw, soccer ball strip, etc. The effectiveness and safety of said response (relating to the projection of power, improved joint safety, etc.) may be evaluated based on the measured spatial relationships of the anatomical points located on the subject's body that comprise the Deceleration Constellation as well as the magnitude of the resulting impulse ("deceleration") forces associated with these actions/points.

According to another embodiment of any paragraph(s) of this summary, the present disclosure's objectives include: teaching and training of safe, powerful kinematics/techniques, to effectively retrain the athlete/subject to more effectively deal with received physical impacts, and to safely dissipate internal forces during reaction-based movements. Other objectives include to develop "impact resistance" via novel joint stabilization training and improved reaction-based performance without the risks inherent in actual physical contact during training.

According to another aspect of the invention, the subject's involved joint(s), for example, the shoulder, elbow, knee, etcetera, may be less susceptible to injuries via this practice of the present disclosure. This practice may also concurrently protect the practitioner from externally received impacts while improving the ability to generate and transfer (impact) power.

According to an aspect of the invention, training is focused on ensuring that the involved joint structures are properly aligned/positioned/"locked down" for the effective and safe transfer of energy through said joints and through the subject's body. Such timely and effective co-contractions of said involved joints, for example, the shoulder joint(s), thereby provide a measure of injury protection. Plus, the forces associated with the deceleration of the hands concurrently with the proper alignment of the involved shoulder joints and the maintenance of a vertical spine may improve performance and reduce the risk of joint injury.

According to an embodiment of any paragraph(s) of this summary, the present invention immerses the subject in the aspects of the teachings herein.

According to another aspect of the invention, while reaction time, acceleration, velocity and CG elevation are all measured during realistic simulations, it is the magnitude and timing of the DC Constellation decelerations and segmental kinematics extracted during simulated game play that are believed to advance the subject's joint stabilization capabilities.

According to an embodiment of any paragraph(s) of this summary, deriving novel performance and kinematic data may serve as the basis for predictive analytics relating to the risk of joint injuries or other orthopedic injury.

According to an embodiment of any paragraph(s) of this summary, known knee baseline and post injury evaluations ignore the contributions of the subject's upper body.

According to an embodiment of any paragraph(s) of this summary, young women who had suffered ACL tears may exhibit more trunk (spine) and upper body movement than either men or uninjured women. Female athletes who injure their ACLs may not adequately "steady" their upper bodies as they move.

According to an embodiment of any paragraph(s) of this summary, the present disclosure characterizes how upper body movements are initiated and coordinated during the execution of sport relevant activities, thereby providing actionable insights and novel predictive analytics relating to heightened risk of brain or orthopedic injury, (concussion or knee, for example) while improving the execution of offensive and defensive techniques.

According to an embodiment of any paragraph(s) of this summary, the simulations taught herein retrain the subject's neuromuscular system while improving sport, or otherwise weight bearing kinematics/technique to more effectively deal with externally received physical impacts, and to efficiently dissipate the internal forces generated during aggressive changes in direction.

According to an embodiment of any paragraph(s) of this summary, the present invention provides a more realistic "virtual" test environment that generates novel metrics for both concussion and lower extremity assessment. Known concussion baseline and post injury assessments leave unanswered the sport relevant performance capabilities and capacities of the subject's upper body/torso, including the core, the arms and the spine. Such capabilities are obviously essential for effective, safe blocking and tackling in football, for example. Such tasks are complex and require the coordination of the subject's sensory, cognitive, neuromuscular/kinesthetic and musculoskeletal systems.

According to an embodiment of any paragraph(s) of this summary, the present disclosure accurately and concurrently characterizes both upper and lower body movement during the initiation and coordination of reaction-based movement, for example, during the execution of simulated football or soccer drills, or activities of daily living.

According to an embodiment of any paragraph(s) of this summary, during this simulated game play, the measurement of whole body deceleration offers metrics relating to the subject's "hitting power", to the effectiveness of the associated technique, and to the status of the subject's neuromuscular system.

According to an embodiment of any paragraph(s) of this summary, the present disclosure offers a sport-specific means for administering gait termination assessments, generating full body deceleration data that may be derived from various sport specific techniques, including simulated football tackling and blocking kinematics as well as performance factors.

According to an embodiment of any paragraph(s) of this summary, predicated on the size, velocity and mass of the virtual ball(s) and their instantaneous position, the subject must strive to assume an appropriate stance to both receive and dampen the imbued forces to "catch" and retain possession of a virtual ball. This "dampening" effort acts to challenge the subject's eccentric muscular systems, as well as reaction time, etcetera.

According to an embodiment of any paragraph(s) of this summary, an unsuccessful attempt to "catch" a virtual ball, may be caused by the inability to sufficiently dampen ("brake") the virtual ball's momentum so as to allow for the "actual" catch and retention of the virtual ball. Success requires a simultaneous stabilization of the involved body joints to introduce a degree of stiffness of the hands, arms, shoulders, body core and legs while assuming a stable stance from which to absorb the "impact" of the incoming ball while maintaining balance. The maintenance of a vertical spine during such activities may offer material benefits.

According to an embodiment of any paragraph(s) of this summary, the present invention may determine both hand position in virtual space and the hand's shape. Examples of hand configurations during training, therapy and assessments include football blocking and tackling, boxing, throwing/returning a ball, grabbing/touching an object in the virtual world, etc. Obviously the "shape" ("configuration") of the subject's hand(s) may differ with each distinct activity/task. For example, the hands may form a fist (closed) for boxing, while they may be opened and lead with the palm to execute a football block or catch a ball. For tackling in football, the arms may open wide with the palms parallel to one another (and perpendicular to the ground) in preparation to "wrap around" the running back.

According to an aspect of the invention, a sport simulation provides a "texture map" of the player's Deceleration Constellation depicting the dynamic pattern of deceleration values and moment to moment positional changes for said key body segments.

According to an aspect of the invention, in contrast to the primacy (emphasis) herein for measuring "deceleration", the obvious alternative metric is acceleration. For example, measuring the acceleration of a punch, block or tackle or an aggressive change in direction answers the questions, "How fast did you punch," or, How fast did you run." However . . .

. . . as virtual targets offer no physical ("mass") resistance as does a real-world punching bag or live opponent, such virtual targets obviously provide no tactile feedback regarding penetration. Nor do they impose the desired stress resulting from the deceleration of the effector to improve joint stabilization. There is no feedback relating to the timing and activation of the real-world player's kinetic chain. Accordingly, emphasizing acceleration may logically encourage/reward the subject for "punching through" the virtual target to maximize the "score".

According to an aspect of the invention, the measurement of acceleration at the "target" may fail to provide sufficient "incentives" to focus, i.e. to assume and maintain proper kinematics while decisively applying deceleration/braking forces to control the technique, and therefore maintain one's balance, as well as other benefits to be described. Absent a vertical spine, balance and power may both be negatively affected.

According to another aspect of the invention, each virtual object (the "protagonist") may be assigned a "Momentum Value" (the product of Mass X Velocity), such as a virtual ball, or an anthropomorphic running back, soccer defender, etc. to therefore "proportionately" challenge the subject. This creates the illusion of proportionately challenging the subject's joint stabilization, as well as the global sensory/cognitive/movement capabilities. For example, the subject may be required to produce sufficient stabilization of his involved joints and body core to successfully "tackle" a virtual running back with the assigned momentum.

According to a further aspect of the invention, each virtual object may be assigned a "task" or "role," for example, an anthropomorphic character, such as a linebacker, or an inanimate object, such as a ball moving within the virtual environment, etc.

According to an embodiment of any paragraph(s) of this summary, taught is an interactive game environment, for example, a football game, where the protagonist (subject), to prevail, must satisfy two game objectives: 1). Exhibit correct technique and proper timing during a tackle of the ball carrier, and 2). Exhibit sufficient deceleration to actually "stop" the ball carrier.

With the present disclosure, a properly aligned and stabilized spine may serve as the foundation/anchor during the application of said deceleration (braking) means to prepare the body to safely dampen the deceleration forces.

According to an embodiment of any paragraph(s) of this summary, in contrast to known interactive full body simulations and interactive physical gaming, for example, such as the Kinect Boxing game, the present invention teaches precisely timed decelerations in close proximity of the "intended target", for example, the opponent's jaw.

According to an additional embodiment of any paragraph(s) of this summary, displayed for the user may be a "wire frame" or similar template for the subject to follow/emulate as she moves in response for the presented cues/visual stimuli. Said wire frame may prompt proper movement such as spine verticality in concert with the deceleration of the hand, proper knee alignment and shoulder stability ("lock down") etc.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF DRAWINGS

The annexed drawings, which are not necessarily to scale, show various aspects of the invention.

DETAILED DESCRIPTION

Figure 2:
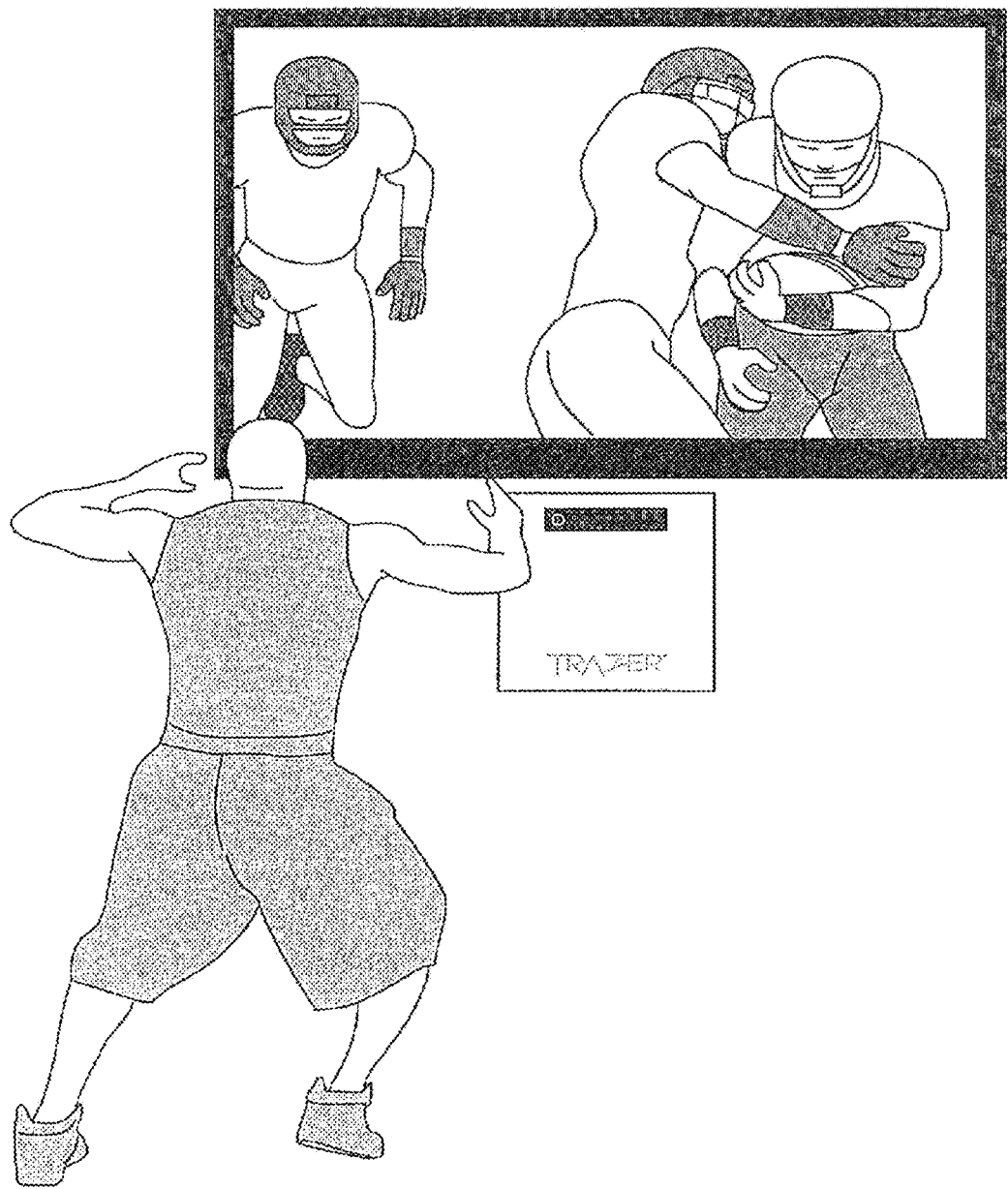
FIG. 2 is a depiction of a participant using a virtual simulation in order to practice a technique used in a contact sport, in this instance, football. Practice of this technique in the real world would require physical contact, avoided with virtual simulation.

Discussed herein is the use of full body simulation to capitalize on novel performance enhancement and joint stabilization methodologies to address the aforementioned identified needs. Reference FIG. 2 of the attached drawings, which shows the subject moving in the real world to control his avatar in the virtual world, to learn techniques, improve form and enhance joint integrity without the risks of physical contact.

The recent confluence of technological advancements in the fields of simulation and human performance/biomechanics was the motivation for the filing of a series of U.S. provisional patent applications.

Explained herein is how the advancements disclosed may materially improve orthopedic, neurological and geriatric assessments, rehabilitation and performance enhancement. Nearly all populations, from elite performers, to aging populations at heightened risk for joint and neurological injuries, may benefit from the simulation-based training delivered by such advancements.

In a realistic manner, these simulations train the subject's (athlete, soldier, senior, etcetera) sensory, cognitive, neuromuscular and musculoskeletal systems to more adeptly deal with received physical impacts, to generate and deliver power as a direct byproduct of precisely timed decelerations of correctly aligned body segments, and for the more efficient resolution (dissipation) of internal forces generated during aggressive reaction-based movements.

Full Body Positional Tracking, Analysis and Predictive Analytics.

The present invention's programming is founded on the premise that prompting spontaneous (reaction based) movement creates more complex and realistic musculoskeletal stresses than either pre-planned or controlled movement patterns/challenges.

The present invention's programming may represent the optimal "environment" to test and train joint stabilization and overall reaction-based performance, to replicate, with unprecedented fidelity, and retrain the performance/execution of the sport/physical performance fundamentals causality of orthopedic and neurological injuries or disease, with a focus on the brain, shoulders, and knees.

Novel performance and kinematic data that will be the basis for predictive analytics directly related to heightened risk of ACL knee or other orthopedic or neurological injuries or disease will be derived.

The present invention's novel training protocols and assessments provide previously immeasurable data regarding the subject's joint and full body stabilization capabilities, balance, kinematics (form) and (sport specific) reaction-based performance. These fundamental performance capabilities for all weight bearing populations are currently unaddressed.

One objective for the training described herein is a reduced risk of injury during game activities that are causality of concussion/brain and orthopedic injuries especially of the shoulder, elbow, knee, shoulder, neck and spine.

Another objective includes assessments offering improved sensitivity, relevance, and authenticity as the basis for predictive analytics relating to performance enhancement and injury prevention.

Discussed herein is the scientific rationale for the efficacy of the assessments and training disclosed.

The present invention provides a form of training without the risks inherent in actual physical contact. It imposes on the subject a demanding movement discipline based on the principles taught herein to mitigate the risks associated with physical contact.

The present invention teaches a discipline where there is no actual physical contact between real world training partners, or between the subject and a physical object, such as a heavy bag. Since no actual physical contact is possible between a real world subject and his/her virtual competitor(s), fundamental to the present invention's utility are novel physical performance metrics (prompting precisely timed decelerations of properly aligned body segments) that are believed to more effectively transfer to real world activities.

All training activities under the present invention similarly teach and practice that the initiating accelerations of an "effector", for example, of the hand, are "abruptly" followed by precisely timed, aggressive decelerations that culminate at a precise location/target in free space to provide a uniquely holistic and functional way of imposing functional "stress" on the involved joint(s), for the purpose of both improving joint stabilization capabilities and reaction based performance.

No externally applied physical resistance is imposed on the subject with this method of training. Rather it is the coordinated braking (decelerating) of the involved joint or joints (for example, the shoulder's antagonist/agonist muscles) and the spinal muscles post acceleration of the hand ("effector") that may generate significant functional "energy"/stress that uniquely and directly benefits the involved shoulder joint.

In addition to improving joint stabilization, the current invention synergistically improves segmental and whole body power production without the risk of exposure to physical contact. This is believed to be a more relevant and authentic physical assessment and training methodology than that currently employed in physical therapy, neurology, performance training/enhancement, etc.

First Embodiment

Currently known means to improve joint stabilization involve isolated capacities, i.e. range of motion and strength drills. As the shoulder joint allows movement in multiple degrees of freedom, challenging all these vectors in a realistic, sports specific (reaction based) manner represents a significant challenge.

Figure 1:
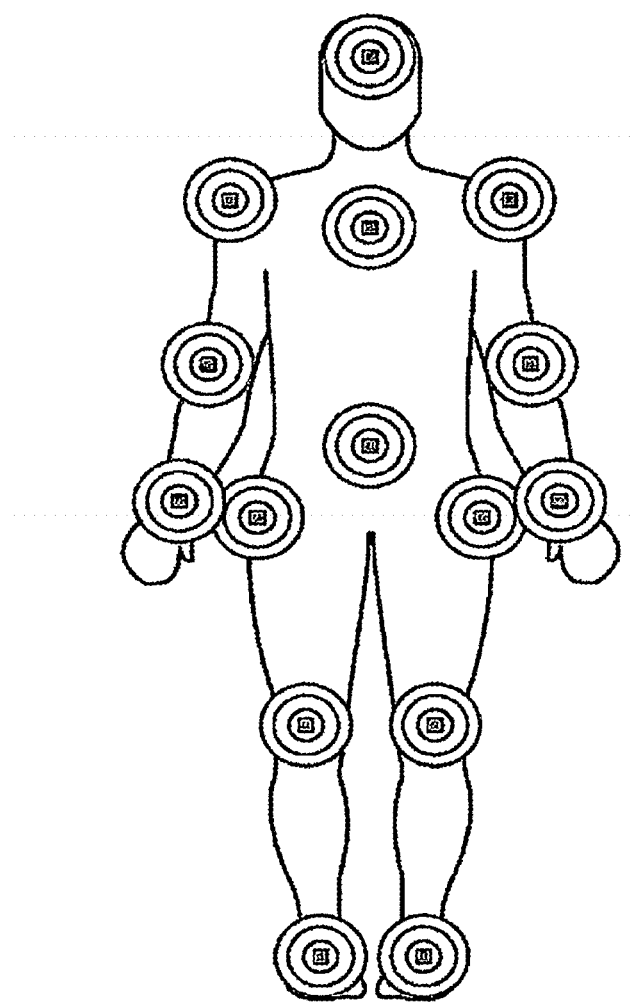
FIG. 1 is an illustration of the approximate anatomical location of the joints that may be tracked during testing or training. The continuous three-dimensional position (X, Y, Z) of each point comprising the subject's Deceleration Constellation (DC) is tracked in essentially real time.

The present invention defines herein the moment to moment spatial and temporal relationship of a cluster ("an array") of anatomical points tracked on a person during interactive testing, training and rehabilitation simulations. With reference now to FIG. 1, the approximate anatomical locations of the points tracked are illustrated. For purposes of this invention, the relevant points for each prompted technique will form the subject's Deceleration Constellation (DC). During testing or training, the continuous three-dimensional position (X, Y, Z) of each point comprising the subject's Deceleration Constellation is tracked in essentially real time.

The current invention's tracking serves to identify postures, techniques, gross body movements, "discrete joint displacements, etc. exhibited by the subject during "game play." Aspects of this invention relate to the rate of force production and whole-body coordination/stabilization and balance, in combination with the concept of precisely timed decelerations.

The present invention teaches means to be applied during reaction-based training at "game" frequencies (higher speeds) and during simulations of the stresses/techniques that said joints may actually experience. It is believed effective for broad populations with all levels of movement capabilities.

The Smooth Transfer of Energy/Power

The present invention creates/delivers interactive, full body simulations that assess the performance/movement of an array of anatomical positions on the subject's body.

The purpose of these teachings is to develop/improve and assess/characterize complex reaction-based functional skills and tasks while concurrently improving reaction-based joint stabilization capabilities. This practice will improve how interrelated body segments and joints synergistically perform to produce the desired movement response/outcome. Such efforts may involve the coordination/marshaling of essentially the subject's entire body.

It's the verticality of the spine and the simultaneous contraction of the core that may accommodate the forces generated upon deceleration to conduct safely through the kinetic chain in order to enhance the performance of the involved joints.

These novel joint stabilization strategies, i.e.: a forceful deceleration at the completion of a technique, as taught herein, protect the involved joints from injury while increasing power generation. For example, the magnitude and timing of deceleration at the completion of a technique ("terminal point"), as well as the kinematics associated with such effort, provide novel and valuable insights relating to joint(s) structure "preparedness" from both the perspective of incurred physical contact as well as from the viewpoint of reaction-based performance capacity.

Plus it is the forces generated by the deceleration of the hands at the target/destination that contribute to the concurrent training of the involved shoulder joint(s) in a uniquely functional manner. The spine, provided it has maintained verticality, may also contribute to the successful transfer of force.

Training with the present invention teaches that the momentary "locking"/"engagement" of an involved joint(s) may act to more effectively stabilize it; for example, during a football player's execution of a block, block destruction technique, or tackle. Note that the present invention's joint stabilization strategies are not tested and trained in isolation, but rather as a continuum of tasks (capabilities) ranging from the ability to recognize and interpret visual information, to the initiation of an effective reaction-based, weight bearing movement/response (such as a virtual world block or tackle), to occupying the "correct" field position at the correct moment in 3D space.

Plus, the motion capture and subsequent analysis of such previously unavailable data directly material to a subject's moment to moment form (technique) and movement data may serve as the foundation for a new generation of powerful predictive analytics, for the purpose of injury reduction, especially of involved joints, as well as enhanced reaction-based performance for broad populations.

Such simulations train the subject's sensory, cognitive, neuromuscular and musculoskeletal systems to more adeptly deal with received physical impacts, to generate and deliver power as a direct byproduct of precisely timed decelerations of correctly aligned body segments, and for the more efficient resolution (dissipation) of internal forces generated during aggressive reaction-based movements.

Full body simulations provide the means to more safely and effectively replicate the decelerating forces imposed on the subject's joints during real world game play, to improve joint stabilization and overall reaction-based performance, by the application/imposition of functional stress on said joint(s).

Another primary objective of the present invention is to provide uniquely functional, reaction based (whole body) means for improving joint stabilization capabilities under a wide variety of (simulated) real world conditions. The objective is to be adoptable and relevant for broad populations: applicable for improving actual game techniques (for example, football blocking, tackling, etc.), for assisting aging populations in navigating their environments, and for whole body strengthening and improvement of joint stabilization in under-used extremities/joints for the bed-ridden.

The present invention measures the deceleration of one or more of the points defining the DC Constellation. Such points may act to determine 1). whether the body segments are properly aligned, 2). the quality (kinematics) of the subject's technique, 3). the "terminal point" of an attack, block, punch, grab or any myriad of other body movements. In one aspect, it may be the instantaneous contraction of the shoulder's (or other joint's) governing antagonistic (i.e. "braking") and agonist muscles following a movement/technique's initiating (ie acceleration) phase.

Figure 5:
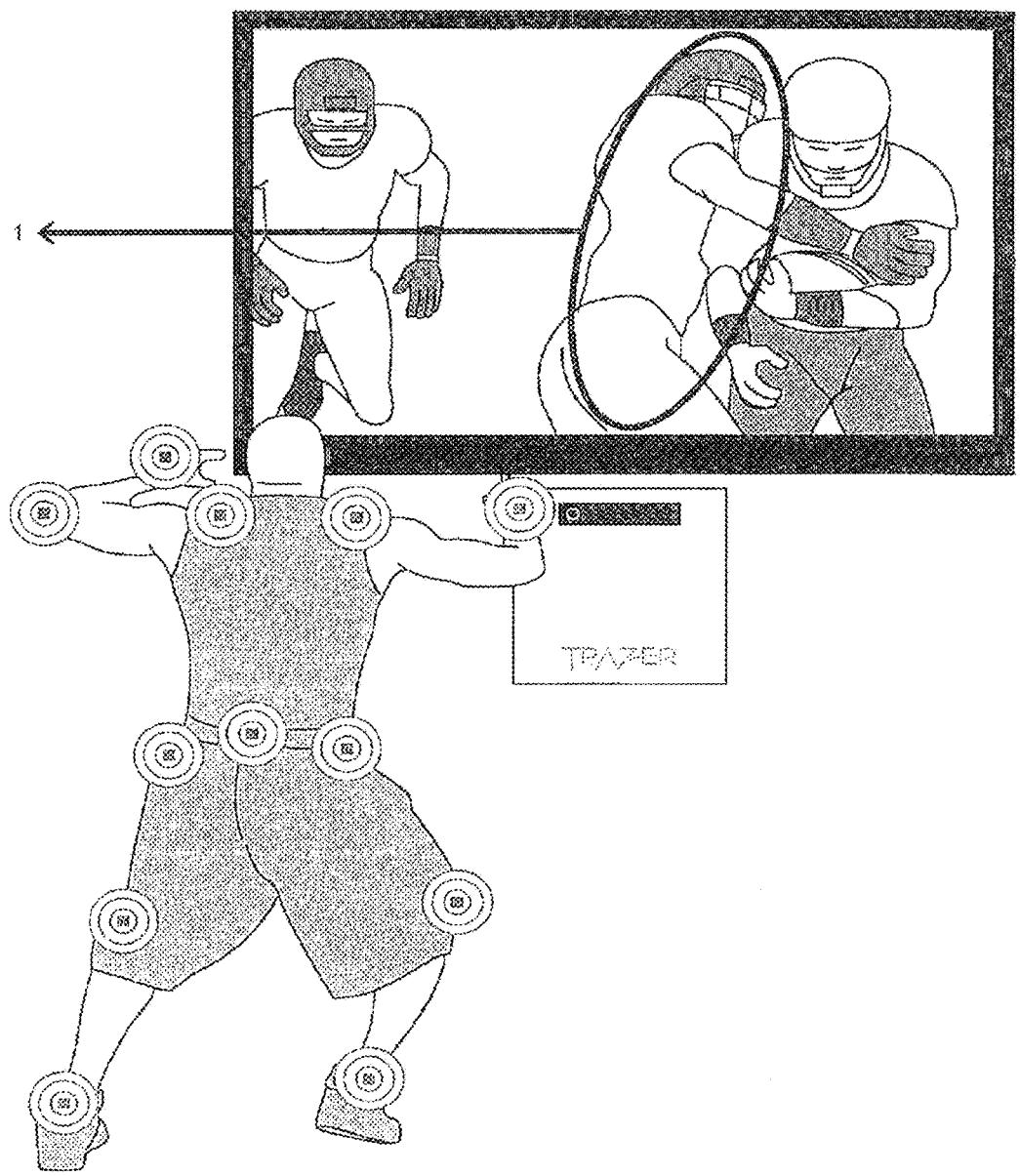
FIG. 5 shows an overlay of the Deceleration Constellation points being tracked on the participant named in FIG. 2. The animation (1) circled on the screen is the avatar of the real-world participant.

Reference FIG. 5, this positional information serves to characterize the player's moment to moment form (kinematics) as well as his physical performance (reaction time, acceleration, velocity, deceleration, etc.) for each body segment tracked. Real Time Data directly relating to joint stabilization and body segmental angles, as well as the associated initiating accelerations and subsequent terminating decelerations associated with the subject's Deceleration Constellation are tracked.

The decisive deceleration of the hand(s), or other effectors while interacting with the interactive activities (i.e.: catching or throwing a ball, tackling or blocking an opponent, moving an on-screen object, etcetera), intentionally imposes forces on the subject that may be de-stabilizing. Taught herein is the training of the spine to maintain verticality, which benefits from a tightening and locking down of the core muscles for support of the spine.

The present invention enables precisely "tailored" forces to be applied to the involved joints for the purpose of both improving reaction-based performance and for reducing injuries. Additionally, any such protocols may act synergistically to reinforce the correct execution of real world technique/behaviors, such as: catching or throwing a ball, tackling or blocking an opponent, moving an on-screen object, etcetera.

The subject, via her avatar, may interact in the game simulations with, for example, her hands, knees, shoulder, elbows, etcetera. For the purposes of this disclosure, some such body parts that interact directly may be described as "end effectors." A term of art also used in robotics; an end effector is the device at the end of a robotic arm, designed to interact with the environment. Reference FIG. 8, wherein the subject's right knee (4) functions as an end effector, as the subject blocks the drive of the virtual opponent.

Spontaneous visual cues may prompt the acceleration and subsequent deceleration of the hand(s) (or other "effectors") to impose relevant, internally generated stress on the involved joint(s) in order to improve joint stabilization and reaction-based performance. The initial acceleration and subsequent timing and magnitude of deceleration of one or both involved hands (or other effectors), as well as related DC anatomical points defining a technique may be quantified. Reaction Time may be measured as well.

With the present invention, reaction-based movement challenges may be "customized" to train essentially all major joints, for example, the shoulders, elbows, hips, knees, and ankles, for roles that may include: linebacker or soccer goalie, etc. Movement challenges may, for example, be applied in a manner that acts to train global aspects of the subject, not solely the involved isolated joint(s).

An important objective for tracking points on the DC is to detect movement/displacements, for example, of the shoulders and other joints. These may include accelerations, decelerations and other displacements resulting from (or coinciding with) the initiating movement and subsequent decelerations of the subject's hand(s) or other effectors. Said tracking may determine whether these displacements are consistent with effective and safe technique. Particularly material in the cited example is to determine whether the shoulders were properly stabilized, as the shoulder antagonist/agonist muscles assist in the decelerating/braking, perhaps described as "anchoring" of the hands. A subject's shoulder performance may be determined, in part, by the magnitude of shoulder vector displacement(s) and the timing of said displacements. In sharp contrast to strength training or other exercises involving isolated capacities, the shoulders benefit via enhanced stabilization capabilities from this application of truly functional stress, which is imposed at game speeds. In each case, the assessment of a technique may benefit from the use some or all points on the Deceleration Constellation.

Brief Summary of Alternative Approaches

Why not "Acceleration" as the primary metric? In contrast to the emphasis (reliance) on "deceleration" taught herein, one widely employed primary metric in sport is acceleration. For example, consider the acceleration of a punch, block or tackle, or of an aggressive change in direction. In the game environment, such as is done with a Kinect boxing game, virtual targets obviously offer no physical resistance as would a real heavy bag or live opponent. Accordingly, there is no tactile feedback upon "virtual contact" relating to the timing and activation of the real-world player's kinetic chain; nor does acceleration provide stress to the shoulder in a productive manner, as does the impulse generated by deceleration. Accordingly, emphasizing acceleration with this type of interactive gaming may logically encourage/reward the subject for "fast hands" and "punching through" the virtual target to maximize his or her "score", but also provide disincentives to maintain the type of technique that acts to improve joint stabilization.

Another benefit of this approach is that it imposes on the subject a discipline that, coupled with correct postures/form, acts to develop/train the eccentric (braking) muscles in sequence/coordination with the accelerating, or concentric, muscles. The known prior art incentivizes/teaches/rewards the subject for "accelerating through" the target. One example of the known prior art is the inventor's U.S. Pat. No. 7,864,168. This patent teaches that " . . . determination of the power of each of the two users is made immediately before a collision in virtual space . . . their power may be simply the product of the subject's mass (which may be entered in prior to beginning use of the system) and the subject's acceleration (determined from the tracked movement of the subject immediately prior to collision." Other relevant examples may include the acceleration of a baseball bat through the strike zone, or a golf club through the ball. In each instance the deceleration of the club/bat post contact with the ball has the energy dissipated over a large arc, thereby considerably negating the positive effects taught herein of deceleration forces on joint stabilization; in this instance the shoulders, elbow and wrist.

With such aforementioned incentive to accelerate "violently", the governing principles taught herein could not be exploited. The measurement of acceleration at the "target" fails to provide sufficient "incentives" to focus, i.e. to assume and maintain proper kinematics while decisively applying deceleration/braking forces to control the technique while maintaining one's balance and improving one's joint stabilization capabilities. And the training taught herein focuses on ensuring that the involved joint structures are properly aligned/positioned/"locked down" for the effective and safe transfer of energy through said joint to the actual target.

Deceleration Forces and "Locking Down"

"Locking down", as referred to herein, is the instantaneous firing of the governing antagonist (braking) and agonist muscles to protect the involved joint(s) (i.e.: the shoulder(s)). For example, the hand ("effector") travels to the virtual target and instantaneously decelerates upon reaching it, locking down the chain of joints between the effector and the ground.

"Locking down" may contribute to the effective, safe transfer of force through the body core, and especially, in this example, to the protection (and strengthening) of the involved joint(s) ("joint stabilization").

This lock down of the involved joint(s) may be concurrent with correct full body posture and correct technique. The maintenance of a vertical spine is believed to be a fundamental aspect for the potency and safety of both upper and lower body movements during the execution of tasks such as football blocking, block destruction, tackling or punching. It may also be fundamental to achieving full body joint stabilization and the associated reduced risk of joint injury.

Furthermore, the correct alignment of the body's kinetic chain during the deceleration phase may facilitate energy flow, as well as the maintenance of body balance throughout execution of the technique.

During game play/training, the subject may be instructed to move explosively (decisively) to "encounter" the virtual opponent via the avatar/surrogate; for example, to practice the defensive move of blocking the path to the virtual goal for the virtual soccer opponent with the ball. See FIG. 8.

At that critical instant of executing a (virtual) block or other such maneuvers, the player may endeavor to assume the stance that maximizes balance, leverage and resistance to impact injury. It is important to maintain upper body verticality (alignment of the spine) while maintaining correct knee position to reduce the risk of knee injury, and to stabilize the involved joints. Sans verticality, there is the potential for an increased risk of knee injuries and ineffective force mitigation.

The Present Invention Tracks the Body in Action

The present invention immerses the subject in realistic offensive or defensive simulations, while concurrently tracking at high speed the subject's Deceleration Constellation. For example, tracking the moment to moment position of the hands may directly influence 3D positional changes of the shoulders to identify a technique.

One objective for the present invention's training is the development of powerful, kinematically correct technique without the physical contact currently required for player development in contact activities. This ability to hone powerful technique in a safe, non-contact (simulated) environment, as taught herein, materially reduces the risks inherent with practice/training, thereby making the practice of hundreds of safe and productive repetitions weekly a viable option. It is believed to be a form of training that translates to actual game or other "real world" environments, Efficient and safe blocking and tackling techniques are identifiable by their characteristic, recognizable movement signatures. Relevant factors include the timing and moment to moment 3-D positions of key body segments, i.e.: the Deceleration Constellation.

The present invention's characterization of both whole body kinematics (form) and physical performance metrics at the moment of "virtual contact" generates novel metrics that are believed to transfer to real world activities with fidelity.

As previously explored, the emphasis is on the timing and magnitude of accelerations and subsequent terminating decelerations of each involved/coordinated body segment at the instant of a virtual tackle, block, block destruction, or other "physical" encounter. This correct application of the present invention is fundamental to its potency, i.e.: the positive results of the training taught herein and its contribution to improving joint stability and reaction-based performance.

There are multiple ways to detect the subject's deviation from a prescribed (desired) movement and/or technique signature. These include but are not limited to: the comparison to prior subject baseline assessment(s) and/or to normative data. Said normative data could be derived from expert/established techniques or movement signatures, etcetera.

Deviations from such previously established movement signatures may indicate a heightened risk of future injury and/or ineffective technique.

"Movement Signatures" Derived from 3D Positional Changes.

FIG. 1 illustrates the approximate anatomical locations of the three dimensional positions (X, Y, Z) of each point comprising a subject's Deceleration Constellation that may be tracked continuously, in essentially real time, during the testing or training taught herein.

This positional information serves to characterize the subject's moment to moment form (kinematics) as well as whole physical performance (reaction time, acceleration, velocity, deceleration, etc.) for each body segment tracked. Realtime data directly relating to joint stabilization, the quality of form/technique and body segmental angles, as well as the associated initiating accelerations and subsequent terminating decelerations associated with the subject's Deceleration Constellation may be reported.

"Movement signatures" for each particular technique/movement may be determined from the aforementioned positional information; for example, a football tackle or block, or a block in soccer. A movement signature may includes a variety of reaction-based movements of the subject including a step, walk, run, tackle, block, kick, strike, hit, punch, push, pull, swing, catch, jump, lung, squat, and throw.

A movement signature may characterize subject analytics relating to a heightened risk of future injury or an existing performance deficit. For example, ineffectual kinematics, absence of a vertical spine, improper knee alignment or inappropriate displacements of an involved shoulder, may negatively impact performance and materially increase the risk of injury, as does the ineffectual practice of joint stabilization. For example, a movement signature may enable the identification of effective and safe blocking, block destruction, tackling and directional change kinematics.

To assist in determining safe return to play status, or progress during rehabilitation, or to correct inefficiencies in movement or form, the present invention may create a motion capture profile that can be replayed to compare to previous player efforts or to an ideal template.

In an "Instructor Mode", a virtual instructor (perhaps presented as a wire frame figure) may "engage" with, or lead the real-world subject's avatar, whose kinematic "shadow" is displayed. The subject's movement performance (or movement signature) may be overlaid on the instructor's "perfect" effort in essentially real time. The subject may then elect, in real time, to emulate/mirror the virtual instructor's moment to moment successful attempts, striving to maintain a synchronous relationship with the instructor avatar to ingrain "perfect" form through reinforcement of proper knee angles, spine/torso position, while stabilizing key joints comprising the Deceleration Constellation.

Program 1: Aging Populations

For Aging Populations, the objectives include the assessment and enhancement of both: 1). dynamic, full body joint stabilization and force production capabilities, and 2). non and weight-bearing, multi-directional, reaction-based movement performance, typically, however, at lower amplitudes/efforts than those sought in athletic populations.

Simulations for aging populations are designed to safely and effectively challenge and "re-engage" the subject's sensory, cognitive, neuromuscular and musculoskeletal systems, with an emphasis on the improvement of joint stabilization and related power generation capabilities.

Protocols for the Aging Populations may enhance the subject's ability to process visual information, and to successfully mobilize/respond while adopting and maintaining effective kinematics and joint stabilization strategies.

For neuromechanically challenged populations, the present invention's form of progressive training/exercise for the Aging may reduce the risks associated with full weight bearing activities as full weight bearing activities may be causality of falls. Expected improvements include dynamic reaction time, balance and multidirectional movement capabilities, reducing the risk of falls and of orthopedic/joint injuries to the ankle, knee, hip, shoulder, elbow, etcetera.

The objectives include: the reduction in the incidence of orthopedic injuries, by both improving the ability to control weight-bearing movement and by dampening and transmitting large forces more safely and efficiently.

Performance measurements include: reaction time, acceleration, velocity, deceleration and positional changes for each or the tracked body segments, via the array of points located on the subject's Deceleration Constellation.

Assessments, as discussed herein, offer improved sensitivity, relevance, authenticity and novel predictive analytics compared with known alternative methodologies.

Novel, Age-Specific Movement Challenges

Simulations for the Aging may, for example, have the subject react to the displayed visual cues and respond with appropriate body movement. These visual cues may prompt the subject to move to a location in the physical training area ("real world") that corresponds to a task ("challenge") in the virtual world. One example would be for the purpose of intercepting ("catching") the target/object ("ball"), the subject would move so that his avatar intercepts the displayed virtual object that may be either stationary or moving. Another might be moving objects in the virtual world from place to place, using principles of momentum, acceleration and deceleration to do so.

Figure 6:
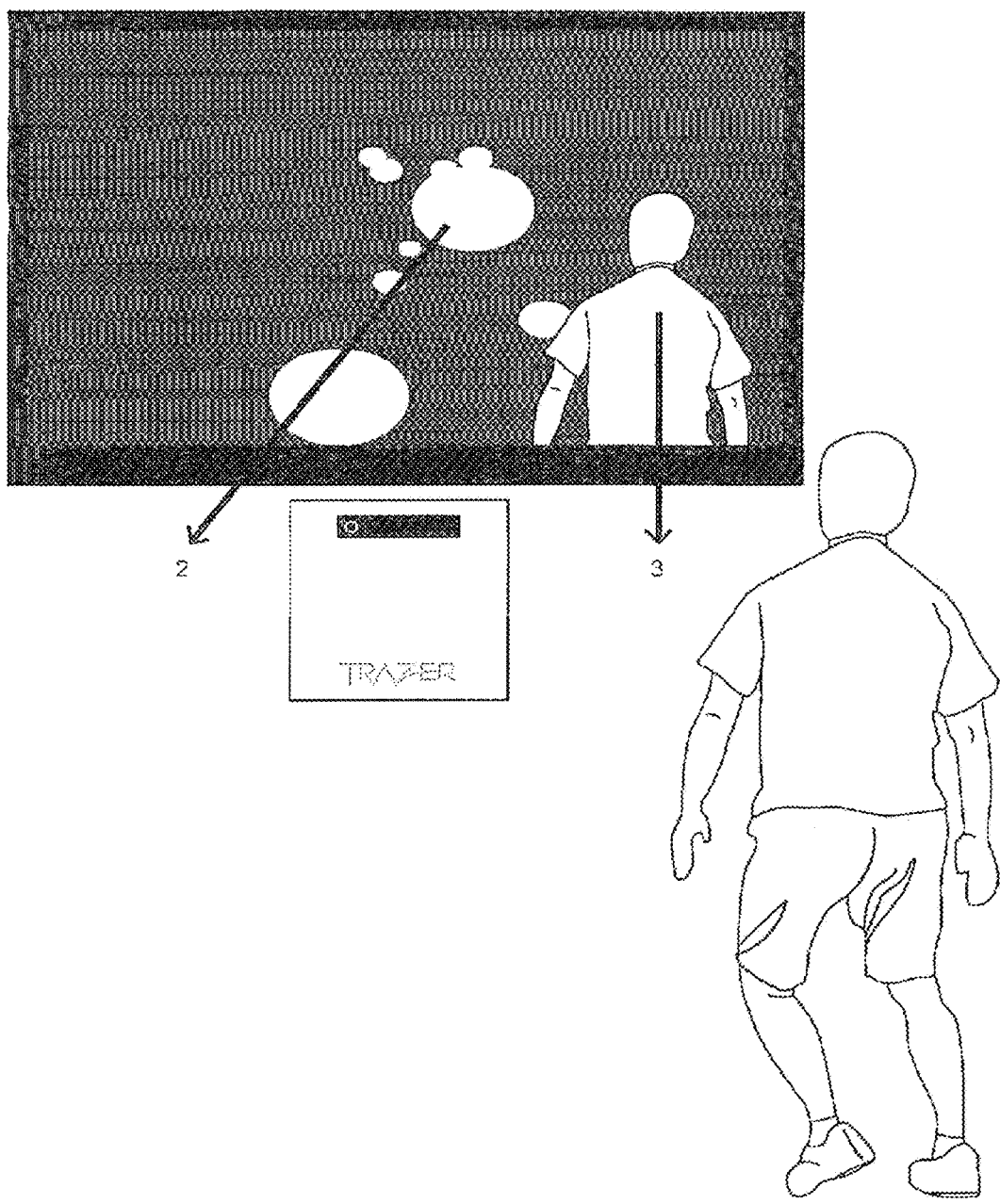
FIG. 6 is a depiction of an aging person engaging in an activity demanding depth perception, timing, and distancing, while practicing appropriate technique for catching and/or throwing a ball in a virtual simulation.

Another example of game strategy has the subject endeavoring to intercept ("catch"), via his avatar, the virtual object(s) introduced on the large display. This Aging program delivers spontaneous (unplanned) visual stimuli that elicit realistic movement responses that challenge, and ultimately improve, full body joint stabilization capabilities. Reference is made to FIG. 6. The subject is moving into position in real space to intercept the target/ball (2) via his avatar (3). He will raise his hands at the appropriate moment and engage the body segments analyzed by the Deceleration Constellation into position to "catch" the virtual ball, or other suitable object. This activity may be engaged in with a variety of technology interfaces, including head-mounted gear.

Yet another game protocol has the subject interacting with the displayed virtual ball(s) in a number of different/distinct body postures predicated on the size, location, momentum and movement characteristics of said virtual ball(s).

Another iteration of the game/protocol objective has the subject visually sense and react to the displayed oncoming virtual ball(s) by moving on the real-world field to a position/location, via the subject's avatar in the virtual world to catch/intercept the virtual ball. Both proper kinematics (form) and joint (activation) stabilization capabilities at the moment of "catching" the virtual ball are exercised. Such activity acts to train/condition the entire body for the more efficient channeling and resolution (dissipation) of both internal and external forces, to improve joint stabilization and enhance power generation and the efficacy of the associated weight transfers of key body segments.

Such imposed body postures and resulting efforts may represent the optimal (most efficient) approach to successfully completing a given task, or alternatively, they may serve as a novel and challenging functional therapeutic exercise. By way of example, when preparing to intercept a virtual ball or other virtual object, each arm of the player may assume its own unique positioning of the hand, elbow and/or shoulder for the purpose of successfully intercepting/catching and/or repelling the virtual ball in 3D space. An imposed task may elicit positioning of the hand, wrist, elbow and/or shoulder of one arm that is diverse at times to the opposing arm of the subject. This diversity of positions may also be expressed by the right and left limbs moving in parallel. In other words, a "two handed" catch or throw. See FIG. 3 of accompanying drawings. This player, in the real world, demonstrates one approach to proper form/posture to absorb the incoming load in a manner necessary to catch a large, virtual ball.

To elicit the desired postures, permutations of game play may vary the virtual ball's origin. For example, if the virtual ball originates from the virtual ceiling, the subject would place each palm toward the ceiling with the elbows pointed toward the floor to catch or repel the downward moving virtual ball. Likewise, if the virtual ball or target emanated from the floor, it could be met with both the palms and elbows extended toward the floor. Of course, innumerable permutations can be developed.

Once in proper position to intercept the virtual ball(s), the subject may vary hand/arm movements that place him (more precisely, his avatar) in a position to either "catch" or "repel" the virtual object. By way of example, to "catch" a fast-moving virtual ball, the subject must move to the correct position on the real-world field, and concurrently position his avatar's hands in 3d space at the proper position and at the precise moment in time to successfully intercept (catch) the virtual ball. To "catch" or repel and subsequently "control" the oncoming virtual ball or balls requires both effective movement capabilities, and sufficient joint stabilization of the points on the subject's Deceleration Constellation.

During "game play" the subject strives to maintain control of his body center of gravity (i.e. via depth of stance), as well as marshal/coordinate the engagement of his involved body segments during prompted, often unpredictable, full body sequences of accelerations, decelerations and directional changes.

Deceleration and "Force Modulation"

Figure 3:
FIG. 3 is an illustration of appropriate technique and joint positioning for catching a ball in the real world. Said technique and joint positioning would be replicated without a real-world ball when the participant is engaged in the virtual simulation.

FIG. 3 illustrates the successful completion of a "catch" in the virtual world. The goal is for the subject to securely "retain" possession of the "caught" virtual ball, i.e. the ball cannot "bounce out of", or "escape through" the (virtual) hands.

Subjects are tasked with gauging the speed and mass of the virtual ball(s) to determine the level of "force reduction", via the adept practice of joint and body stabilization, required to successfully "catch" the virtual ball, preventing it from hitting his/her avatar's body, while simultaneously endeavoring to prevent the "ball" from "bouncing" out of the subject's hands. Thus, the objective is to achieve a balance between dampening the incoming force and exerting sufficient resistance to prevent either of the aforementioned undesirable outcomes from happening. This effort would obviously benefit from an introductory practice session to become accustomed to the required sensitivities.

FIG. 6 illustrates one iteration of the game/protocol objective wherein the subject visually senses and reacts to the displayed oncoming virtual ball(s) by moving on the real-world field to a position/location, via the subject's avatar (3) in the virtual world, to "catch" the virtual ball (2), all while demonstrating both proper kinematics (form) and full joint (activation) stabilization capabilities at the moment of "catching" the virtual ball. This type of activity may train/condition the entire body for the more efficient channeling and resolution (dissipation) of both internal and external forces, thereby improving joint stabilization, as well as enhancing power generation and the efficacy of the associated weight transfers of key body segments.

All these benefits may be derived by the subject during his ambulation/navigation of simulated environments to accomplish the complex physical tasks taught herein.

Virtual Objects that Serve as "Protagonists" May be Assigned a "Momentum Value."

"Momentum" (the product of Mass X Velocity) may be assigned to each virtual object/protagonist, such as an anthropomorphic running back, soccer defender, etc. to create the illusion of proportionately challenging the subject's joint stabilization, as well as global sensory/cognitive/movement capabilities. For example, the subject may be required to produce sufficient stabilization of his involved joints and body core to successfully "tackle" a virtual running back with the assigned momentum.

For example, as shown in FIG. 3, the subject is required to produce sufficient stabilization capabilities of his involved joints and body core (Deceleration Constellation) to successfully "catch" and "retain possession" of a virtual ball with the assigned momentum.

Undertaking Effective Kinematics

To be successful, the subject must assume an effective pose (posture) that places his hands in a position in 3D space at the precise instant of time that would allow him (actually his avatar) to actually "catch" the ball. Characterization of full body kinematics provides critical performance/positional data and kinematics regarding the "virtual catch". The subject will fail to "make the catch" if the body points tracked on his Deceleration Constellation confirm that he would not have successfully caught and retained possession of the virtual ball.

Integral to each "catch" is the dampening/absorbing of the impact forces, which can be accomplished, at least in part, by the effective joint stabilization associated with the points represented by the Deceleration Constellation. Proper stabilization acts to protect the subject's involved joints while ensuring a more efficient transfer of energy through the subject's body into the "ground."

Dampening Momentum to Retain Possession; Improving Stabilization Capabilities.

An unsuccessful attempt to ("hold onto the virtual ball"), may be caused by the inability to sufficiently dampen ("brake") the virtual ball's momentum so as to allow for the actual catch and retention of the virtual ball. Success may require a simultaneous "locking down" (the firing of the involved body segments to introduce a degree of joint stiffness) of the hands, arms, shoulders, body core and legs while lowering the center of gravity and assuming a stable stance from which to absorb the "impact" of the incoming ball while maintaining balance.

Verticality of the Spine.

The subject's success at catching the virtual ball may be partially dependent on his ability to control his body core and to maintain verticality of his spine. Abrupt contraction of the core at the apex of deceleration may assist in the maintenance of a vertical spine, in addition to locking down the constellation of involved joints. Alternatively, an unsuccessful attempt may be the result of the subject assuming a positionally correct but rigid and unyielding posture. This rigid but unyielding posture would fail to lock down the involved joints and to sufficiently "dampen" the ball's inertia, with the result that the "ball" bounces out of his hands.

Predicated on the size, velocity and mass of the virtual ball(s) and their instantaneous position, the subject must strive to assume an appropriate stance to both receive and dampen the imbued forces to "catch" and retain possession of a virtual ball. This "dampening" effort may also challenge the subject's eccentric muscular systems.

Associated objectives include the assessment and improvement of visual reaction time, multidimensional movement capabilities and effective joint stabilization.

An alternative approach has a virtual ball small enough to "catch" with one hand, given proper body position and mechanics on behalf of the subject. A small virtual ball possessing significant momentum may especially challenge the subject attempting to catch the ball with one hand. Exercising proper stabilization strategies, for example, "locking down" the shoulder of the involved arm, becomes particularly important.

In some instances, the ball may possess/exhibit little momentum due to low mass and/or low velocity; and therefore, could be successfully caught without dampening of the momentum-generated forces. In this example, the subject's ability to safely dampen/accommodate these imposed forces may not be adequately challenged. The subject, for example, may not be compelled to apply joint stabilization principles to negate the ball's momentum. Thus, "adjustability" is important to accommodate a potentially wide range of representative users.

Other material factors relating to the difficulty level of the task may include the number of balls concurrently appearing on the virtual field, the distance and path each one travels, and the frequency/rate of their launch/introduction into the virtual environment.

Adjunct Training Approach; "Hot Potato!"

Figure 4:
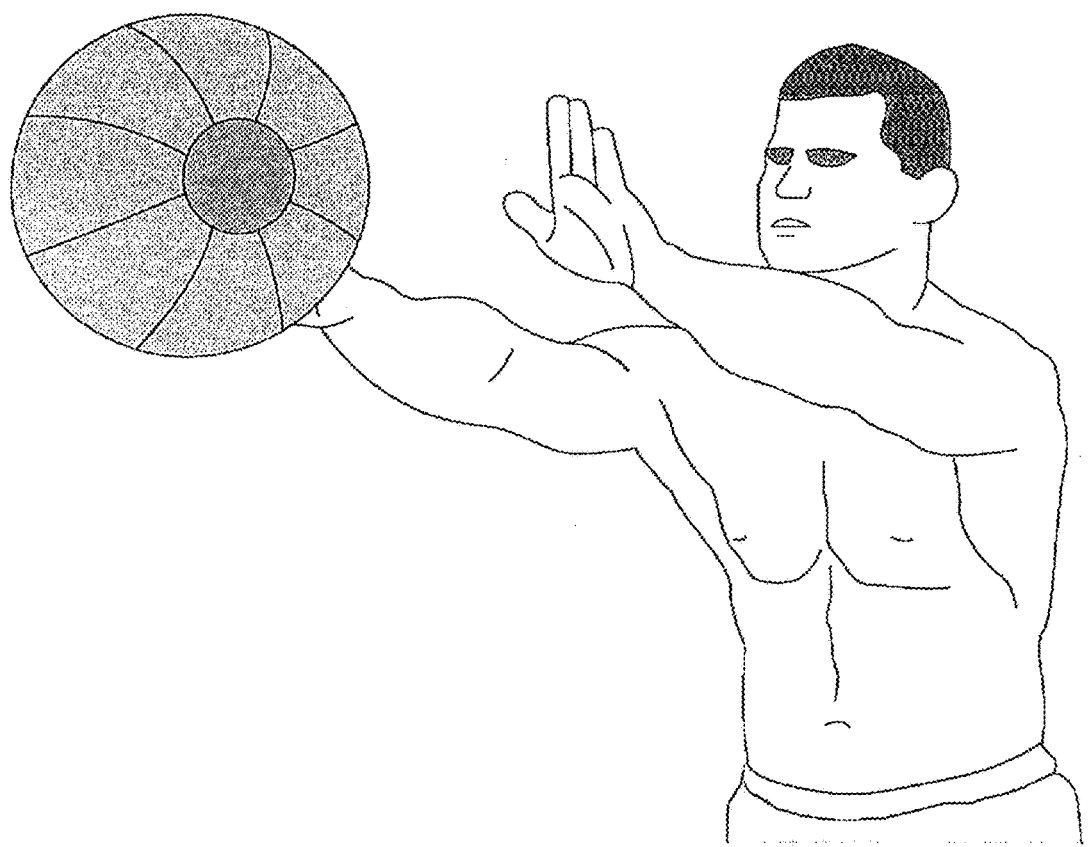
FIG. 4 is an illustration of appropriate technique and joint positioning for throwing a ball in the real world. Said technique and joint positioning would be replicated without a real-world ball when the participant is engaged in the virtual simulation.

Alternatively, the training protocol may have the subject instantly "returning the ball" once it is stopped or caught. In aging populations, the preferred means of returning the virtual ball may be "thrusting" (pushing) with both hands rather than a one arm throwing motion, as illustrated in FIG. 4. This thrusting action may further challenge and develop full body stabilization capabilities, as the body segments associated with the Deceleration Constellation must act in a coordinated fashion for the resultant return to be both powerful and accurate.

Such a "push" (return) of the ball introduces a potentially powerful concentric movement, while concurrently engaging the subject's stabilizing muscles, especially the shoulders. For example, the "return" of the virtual ball could be the result of a high impulse "strike/hit" movement or a lower impulse "pushing movement," thus challenging joints that may include the shoulder, elbow and wrist.

Example of a Suitable Virtual Environment—"3-D World" (3DW)

The following presents one example of a suitable game environment, identified herein as the "3DW environment", now in the public domain and previously employed by the inventor.

The 3DW Protocol. What a subject sees on his computer screen or TV does not change based on where the subject is physically located in the room. Such displays can be characterized as "portals" into a digital world. Now compare the subject's experience while looking through a "portal" to the outdoors, i.e., a window. Where the subject is positioned in the room determines what is seen through the window. For example, being physically close to the window provides a more panoramic view of the outdoors than being positioned a further distance from the window. A shift in position in the real-world room changes what the subject sees, for example, city lights in one direction, a mountain range in the other. With this 3DW gaming technique, the real world playing field links to the virtual world via a wire frame that shifts the entire virtual environment in response to the subject's physical position in the real-world exercise area.

Functioning like a real-world portal, with 3DW, a subject can simply shift physical position to "look around" or "at the side of" or "the top of" or "bottom of" a virtual 3D object to glean location-based visual information. For example, a blue 3-dimensional sphere traveling toward the foreground may have a green dot on one of its surfaces that is only viewable from a certain location in the exercise area.

These 3DW techniques provide the means to embed location-specific visual information that is selectively viewable based on the player's moment to moment physical location. The present invention provides true perceptual-cognition-kinesthetic linkage challenges; the benefits are numerous.

Dynamic 3D visual cues can be delivered to the subject in a wide variety of shapes and sizes, at varying speeds, and with innumerable content possibilities. A subject must locate to the correct position on the exercise field to view such "mission critical" information.

Figure 7:
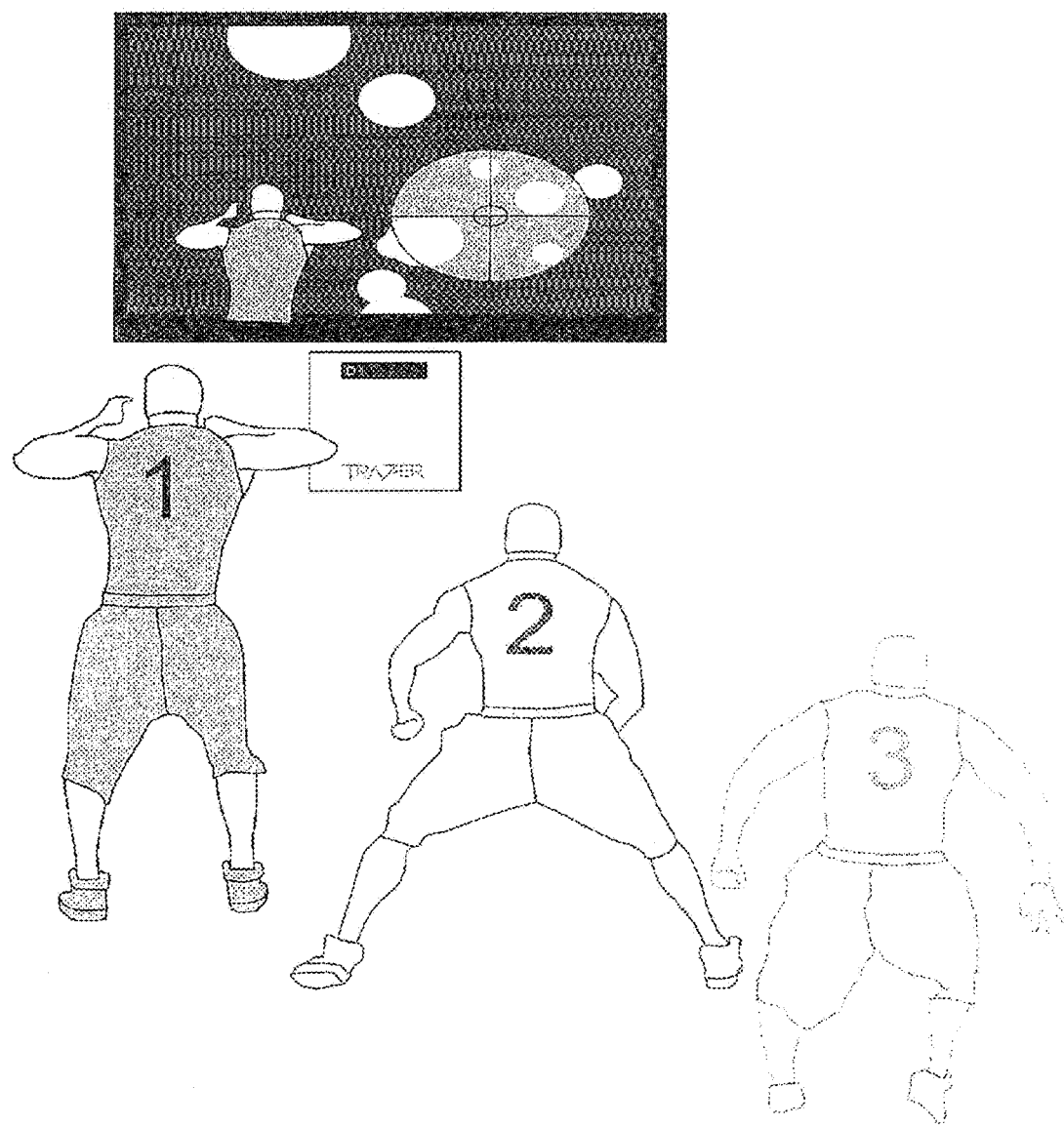
FIG. 7 is a depiction of a participant engaged in a highly neurocognitive activity that also requires movement in free space and appropriate technique and positioning in order to complete the task demanded by a virtual simulation.

In one example, as shown in FIG. 7, each surface of a 3D object presented in the virtual world, such as a cube, sphere, or even an anthropomorphic figure, such as an opposing player, etcetera, can display unique visual information. If the subject moves to the corresponding locations on the "playing field", he can view the front face, top, bottom, or two side surfaces (the back would not be viewable unless the object was spinning) to see all possible "embedded" information on said virtual object. Purposeful movement allows the subject to observe the visual info to solve a game challenge, practice safe movement patterns and similar.

Imagine a Frisbee floating with symbols on top and bottom, viewable only by the player's elevational changes, in order to see the top or bottom of the Frisbee. Virtual objects may continually transit from background to foreground; such as with ping pong, tennis, a baseball in a batting cage, etc. The subject can elect, for example, to either "catch" or "avoid" these virtual objects.

To enhance the entertainment quotient, realism and effectiveness of the programs taught herein, 3DW creates the illusion that the view of the virtual environment, instantaneously, and with fidelity, shifts to reflect the subject's position in the real world.

3DW virtual objects are governed by user-modifiable behaviors; behaviors that enable scaling of the visual challenges as well as a heightened sense of realism. Some of the variables that can be employed in 3DW Challenges include:

Posing of academic problems to be solved by selection of a moving object; for example, 2+3=_____ would require the subject to "catch" an object with a 5 displayed. A picture of a CAT would require the player to catch moving and spinning letters and place them on a grid to spell CAT.

Examples of variables that may enhance both the entertainment value and the therapeutic value of a 3DW method of delivery may include: rate of transit of the object(s), either at a constant velocity or at a speed that varies over the distance traveled; vector of transit (background to foreground, diagonal, etc.) of the objects; shape, size, color, number of objects displayed; spin/rotation of the objects as they travel; presentation of objects in identifiable patterns for pattern recognition drills; view/direction-specific visual information selectively viewable based on the player's real time physical location.

Knee Injury Prevention and Performance Enhancement

There's a widely recognized need for improved methods of preventing knee injuries. Knee injuries are a most visible threat to safe sports participation, especially for female athletes.

Knee injuries are observed in all activities involving aggressive cutting, jumping, landing and/or pivoting. The present invention offers protection from lower extremity orthopedic injury via simulations that replicate, with unprecedented realism/fidelity, the performance/execution of reaction-based sport fundamentals causality of orthopedic injuries, with a focus on the knee, hip, ankle and upper extremity.

Known knee baseline and post Injury evaluations ignore the capabilities of the subject's upper body. Seminal research has concluded that young women who had suffered ACL tears exhibited more trunk and upper body movement than either men or uninjured women. Such upper body movement resulted in much greater pressure on the planted knee, acting to eventually collapse inward the overloaded ACL. A common lack of ability in the core of the body to control deceleration and acceleration in 3-D space has been shown in injured female athletes. Simply stated, female athletes who injure their ACLs may not know how to adequately "steady" their upper bodies as they move.

The present invention also characterizes how upper body movements (adhering to verticality of the spine) are initiated and coordinated during the execution of sport relevant activities, thereby providing actionable insights and novel predictive metrics relating to heightened risk of brain or orthopedic (for example, knee) injury, and improving the execution of effective and safe offensive and defensive techniques.

Knee injury prevention and return to play programs, as taught herein, offer both planned and unplanned simulations. These include choreographed movement patterns where the subject must remain in synchronization (move in concert) with a "virtual coach" or her virtual opponent, thereby delivering reaction-based movements that challenge the subject's performance capabilities, or interactive-unplanned movement challenges where the virtual coach/competitor is unpredictable in her actions, thereby introducing additional sensory and cognitive demands/load on the subject.

Figure 8:
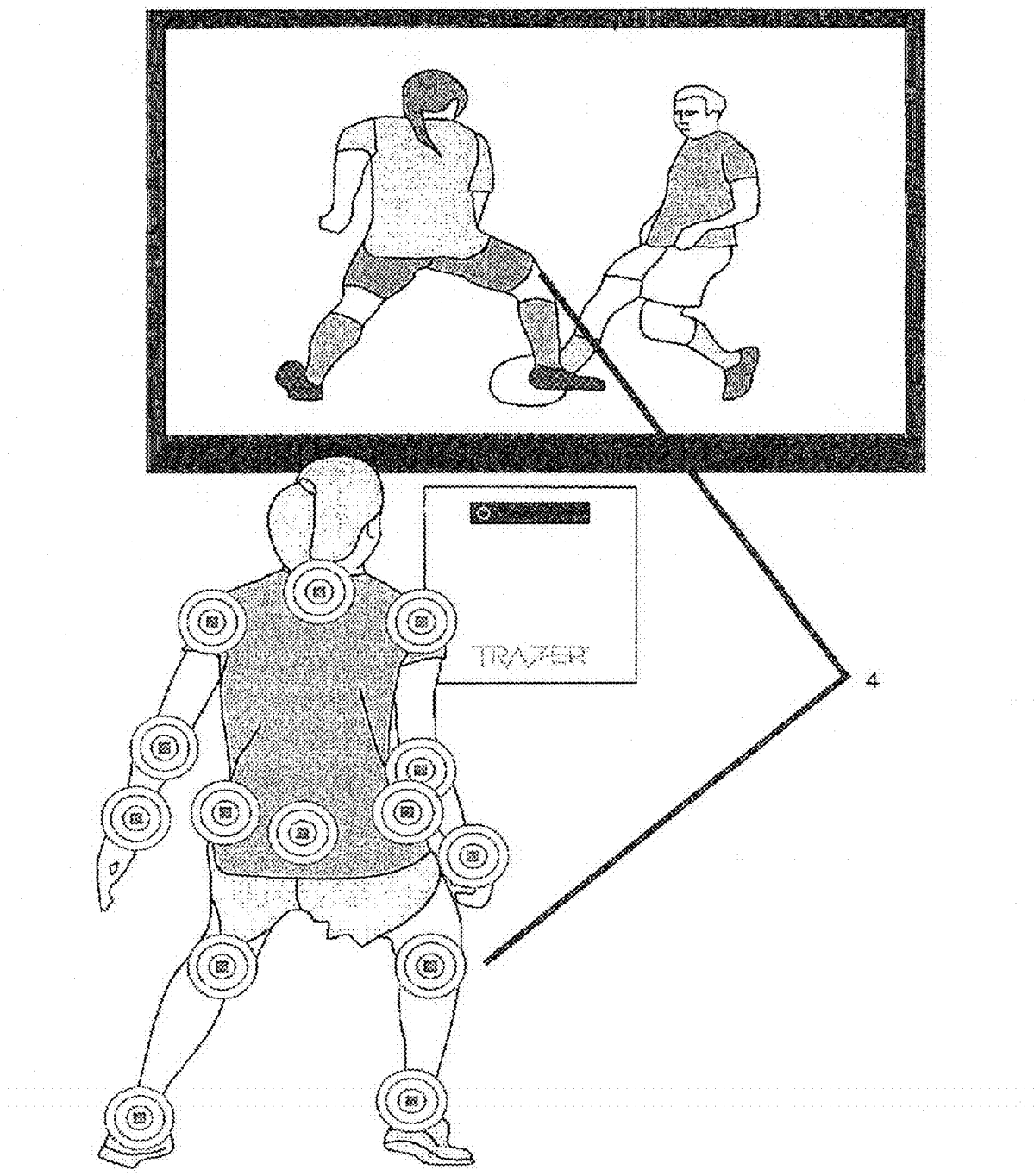
FIG. 8 is a depiction of a participant in a contact sport, in this instance, soccer, practicing proper technique for engagement, using a virtual simulation. The verticality of the subject's spine and correct position of the knees may reduce her risk of a lower extremity injury.

In FIG. 8, for example, during game play, the subject is instructed to move explosively and use her knee to decisively block or otherwise engage with her virtual opponent via her avatar. She may, for example, practice the defensive move of blocking the path to the goal for her virtual opponent by concurrently braking/stopping "violently" by decelerating her body while maintaining correct form/kinematics at the precise moment in time and (virtual) space of executing the block. In each case, the subject endeavors to practice the invention as taught herein at the "terminal point" of her kinematically correct response to assume and maintain the stance that maximizes her stability/balance, leverage and resilience to impact (joint) injury.

During this simulated game play, the measurement of the subject's deceleration forces, in concert with profiling the subject's kinematics at (virtual) impact, provides novel and illuminating insights regarding a subject's neurological and orthopedic health. Especially joint stabilization with focus on the knee and shoulder.

Simulations taught herein retrain the subject's neuromuscular system while improving sport-relevant kinematics/technique to more effectively deal with externally received physical impacts, and to more efficiently dissipate the internal forces generated during aggressive changes in direction.

Realistic Test Environments and Novel Metrics for Concussion and Lower Extremity Testing Known concussion baseline and post injury assessments leave unanswered the sport relevant performance capabilities and capacities of the player's upper body/torso; specifically the arms. Such capabilities, by way of example, are obviously essential for effective, safe blocking and tackling in football. Such tasks are complex and require the coordination of the player's sensory, cognitive, neuromuscular/kinesthetic and musculoskeletal systems.

As background, a simple measure of upper limb coordination integral to the concussion assessment tool SCAT 2 (now SCAT 5) is the "timed finger to nose task" (FTN). Recent literature documents that the FTN test should continue to be used to correlate with normative values in assessing neurological function for sports-related concussion. This FTN protocol is obviously quite limited; it neither assesses sport relevant movements nor delivers objective metrics. Plus, it fails to challenge the subject's cognitive reserves. However, it does appear to confirm the value, no matter how primitive, of evaluating the performance of the arms (torso) post brain injury.

The current invention accurately and concurrently characterizes both upper and lower body movement during the initiation and coordination of reaction-based movement, for example, during the execution of simulated football, soccer, basketball drills, etcetera. Football specific kinematics and performance factors associated with blocking, block destruction, tackling and aggressive directional changes may be more accurately characterized/assessed.

During this simulated game play, the measurement of whole body deceleration offers metrics relating to the player's "hitting power" and associated/governing technique, in addition to reaction time, movement speed, etc. The result is a novel and realistic means to quantity the player's nervous system responsiveness post-concussion, data precisely relevant to a player's current status and susceptibility to both orthopedic and brain injury.

Detecting "Altered Gait Termination Strategies Post Concussion"

Gait termination is governed by the anticipation, control and termination of the forward momentum of the body's core. Recent literature documents that this process is controlled by the central nervous system. Conventional Gait Termination (GT) assessments typically use ground force platforms in laboratory settings for concussion return to play assessments and similar. A recent study sought to identify acute and lingering motor control strategy alterations post concussion via gait termination. They found that even though all concussed participants had reached their baseline values on standard clinical concussion assessments, their braking and propulsion forces continued to be altered, as determined by their gait termination. For a minimum of 10 days post injury, even though all aspects of the traditional clinical assessment had been satisfied, there was a noted alteration in gait termination performance, independent of gait velocity.

It is believed that the present invention taught herein offers protocols that may transform a traditional Gait Termination Assessment into a activity-based/sport specific, "full body scan" via reaction based simulations of actual sport specific and/or activities of daily living scenarios, such as football tackling, thereby providing illuminating insights regarding a subject's neurological and orthopedic health.

The present invention creates an activity specific means for administering gait termination assessments, via full body deceleration data actually derived from simulated activity specific kinematics and performance factors.

Training Joint Stabilization.

The present invention's interactive environment delivers reaction based programming for the purpose of developing effective joint stabilization strategies ("joint health") by imposing precisely timed, internally generated stress on the involved joints. The principles taught herein are believed equally applicable for rehabilitation and training programming for all weight bearing populations, including for aging populations.

To effectively train joint stabilization capabilities via the principles taught herein requires that a properly timed, "real world" force be applied/delivered to the subject's involved joint or joints. By way of example, it is beneficial that both the hand and the involved joint (for example, the shoulder) are in proper position at the moment of deceleration (i.e.: "the virtual impact"). Timing is critical as is the joint's 3-D position in space in order to precisely impose internally generated stress on the involved joint(s).

The foundation is the counterintuitive, diligent practice of, the present disclosure, i.e. the precisely timed "deceleration" of an array of properly aligned body segments at the "terminal point" of an attack, block or other technique.

This application of adeptly coordinated deceleration forces may precisely impose on the involved shoulder, or other joint, more relevant sport/activity specific type forces that are more accurate analogs of real world activities than are the conventional range of motion drills, strength training and similar.

Plus it is the forces associated with the deceleration of the hands at the target/destination that contribute to training joint stability in a uniquely functional manner. The spine, especially if it has maintained verticality, may also be fundamental to this effective transfer of force. It is the referred effects of the decelerating "effectors", for example, the hands, as they reach their intended targets, that uniquely contribute to the coordination and strengthening (joint stabilization) of the shoulder joint(s) and their reliance on the verticality of the spine.

By protecting the involved joint(s), this practice may also act to protect the subject from externally received impacts while concurrently increasing the ability to generate and transfer (impact) power.

Such practice may also improve the subject's "proprioception", "the sense of the relative position of neighboring parts of the body and strength of effort being employed in movement."

Tracking Gross Body Movement ("Them") Vs Full Body Kinematics and Sport-Specific Fundamentals ("Us")

Presently, there are several known companies providing on-field, player location tracking. Examples include Zebra Technology and Catapult. Such location tracking, however, differs radically from the present disclosure and its measurement and training of kinematics and sport specific fundamentals.

These on-field tracking sensing systems measure whole body accelerations, velocities, decelerations, distances, directions, etc. while the tracked player(s) move around the field during a game or practice. Obvious benefits derived include metrics related to the detection of overtraining and the evaluation of conditioning programs.

Such systems, however, say nothing, in sharp contrast with the present disclosure, about the athlete's form (kinematics/joint positions, individual hand/arm/foot speed) and how their body segments coordinate to maximize both safety and sport specific performance. Nor do they assess performance or kinematics of sport specific tasks such as blocking and tackling.

By contrast, the present disclosure's metrics provide novel insights into the player's susceptibility to orthopedic and brain injury during both intentional or unintentional player physical contact, as well as the player's whole body "impact power", which is both measured and trained as taught herein. The coordination/timing and performance of key body segments provides previously immeasurable "context" to these measurements. For example, a player's hand or arm speed could readily be measured via a single accelerometer housed in a wrist band. Hand speed, without accounting for the contribution of the player's body, says little about "stopping power", kinematics or joint alignment and stability. A single arm moving in isolation would obviously be limited in its effect compared with the efficient marshaling of the entire body. This is especially obvious during the practice of football block destructions, tackling, etc.

Plus, as discussed prior, the measurement construct of "acceleration", in isolation, may have material limitations. With the present disclosure, the characterization of a cluster of key anatomical points provides both novel positional and performance information directly related to whole body impact energy and the safe execution of sport-specific fundamentals to reduce the risks of joint injuries.

Testing, Training and Injury Prevention

In summary, the current invention teaches and trains effective kinematics (form) and performance strategies while concurrently improving joint stabilization capabilities to materially reduce the risk of joint and other orthopedic injuries. Benefits may include the: mitigation of the forces associated with externally received physical impacts/insults (a collision), generation and delivery of (impact) "power" as a direct byproduct of precisely timed accelerations and subsequent "violent" decelerations of correctly aligned body segments, and more efficient resolution (dissipation) of internal forces generated during aggressive reaction-based movements, to reduce, for example, the risk of an ACL knee injury during abrupt braking or changes of direction.

Reaction-based training coupled with the maintenance of verticality (an erect posture) of the spine facilitates the forces associated with the decelerations of the hand(s) to: 1). Provide holistic training of the involved shoulder joints in a more realistic fashion to reduce the risk of injury, and 2). to improve functional power and reaction times.

Data Generation

This real time positional tracking of the individual points defining/comprising the DC constellation/array is the foundation for the protocols and measurement constructs taught herein. Most pertinent, testing, as taught herein, offers novel metrics related to both joint stabilization and the resulting functional performance capabilities. The data generated may drive programs to improve reaction time, eccentric muscle activation and full body kinematics.

The assessments taught herein also generate data relating to functional cardiac response, reaction time to both planned and unplanned visual stimuli, mechanical power, and the variability, consistency, and skill of movement in any movement vector.

Such novel applications and principles, as taught herein, can be successfully delivered via a wide variety of assessment, rehab, performance enhancement and gaming formats presented via suitable virtual environments. The TRAZER simulator (www.trazer.com) is one example of suitable hardware means to deliver the capabilities taught herein.

Suitable venues for delivery of the current invention's myriad of programming may include training rooms, clinics, gyms, senior facilities and similar points of service delivery.

Various Game Protocols/Strategies

Choreographed movement patterns include those wherein the subject/athlete must remain in synchronization (move in concert) with a "virtual coach" or a virtual opponent while adhering to proper form (spine verticality, etcetera). Realistic, reaction-based movement responses that more fully challenge the subject's "real world" performance capabilities are elicited. Task-relevant joint stabilization capabilities may be a material aspect of such training.

Another protocol/strategy may involve interactive, unplanned movement challenges where the virtual coach or competitor is unpredictable in its actions, thereby introducing additional sensory, cognitive and neuromuscular/musculoskeletal demands/load on the subject.

In one example, the real-world subject may be "immersed" in realistic offensive or defensive simulations while his/her movement may be continuously tracked via the anatomical points on the Deceleration Constellation (DC), in essentially real time.

With each repetition, the subject may be instructed to practice DC at the "terminal point" of his/her kinematically correct action/response, i.e. to concurrently maximize the deceleration forces associated with the array of body points defining the Deceleration Constellation. Example virtual tasks may include: at the instant of a ball strip, a block, a punch, or other "physical" encounter in the virtual world.

The precision (accuracy) of the effector (for example, the hand) movement in 3D space when responding to the prompted technique, and the associated initiating acceleration of said hand movement, may terminate via a deceleration that acts to challenge/stress the subject's involved joints, for example, the shoulder(s).

The subject may strive to maximize "terminal" deceleration, not acceleration, upon reaching the target. This practice is believed to be distinct from known gaming or other interactive systems.

Other relevant factors may include the efficiency ("linearity"), where appropriate, of the movement path undertaken.

Such metrics as the timing and magnitude of the initial acceleration, for example, of the subject's fist or palm as it moves toward the (virtual) target and then, of its "decisive" deceleration (impulse) as it terminates upon approaching (before actually reaching) the virtual target, provide valuable data regarding joint stabilization/performance of the involved joints.

Further Anticipated Benefits of Training as Taught Herein.

Training benefits include improved techniques/kinematics, movement power, reaction times, enhanced physical conditioning and reduced risk of injury via improved joint stabilization capabilities.

The current invention trains and evaluates the subject's abilities to: process and act upon visual information, utilize sensory/cognitive skills (dynamic reaction time), undertake the optimal pursuit path by choosing best angle/direction (acceleration, velocity), assume and maintain "optimal" full body kinematics consistent with the offensive and defensive role that is currently being tested or trained, while resolving physically demanding, sport relevant challenges via effective application of the teaching herein, i.e.: properly timed accelerations and decelerations through concurrent execution of proper kinematics.

By way of example, for football specific training in this manner, the subject may be instructed to: assume and maintain correct football form (technique) while moving; to approach the virtual ball carrier via the avatar; i.e. head, torso/spine, legs/knees and especially the arms must be properly positioned to execute the tackle, (or for block destruction, etcetera). At the instant of (virtual) contact, decisively contract/activate the relevant muscle groups, i.e. the braking/antagonistic muscles, while adhering to proper tackling form. At "contact" "violently decelerate in a coordinated manner" while maintaining proper form to practice and perfect decelerations of key body segments. At this moment of "impact", the present disclosure characterizes ("captures") in real time the "movement (hit) signature." Upon completion of this virtual tackle, instantly "relax."

Post training, graphical and numerical feedback is provided, which includes movement templates illustrating proper techniques and any differences from those templates by the subject's actual efforts. Kinematic and physical performance data may include joint angles, reaction time, accelerations, etc.

A full body "texture map" of the subject's Deceleration Constellation depicting the dynamic pattern of impulse/deceleration values and moment to moment positional changes for key body segments may be presented.

Though Reaction Time, Acceleration, Velocity and CG elevation are all measured by the current invention, it is the magnitude and timing of the decelerations and performance related segmental kinematics extracted during this simulated game play that contribute the novel metrics relating to both safety and efficacy. The resultant metrics are uniquely transferable to actual play, with anticipated unprecedented improvements in accelerations/decelerations, balance, stability, joint stability and safety, etc.

The derived performance and kinematic data may be the basis for predictive analytics directly related to the heightened risk of orthopedic and brain injury, to empower return to play (rehab) assessments and sport specific performance enhancement and injury prevention programs.

Additional relevant performance factors for the real world subject may include: Was the strike/technique accurate, i.e.: did it hit the intended target? Was the technique practiced technically correct? What was the deceleration of the strike/technique upon reaching the virtual target? One objective may be to maximize deceleration at said endpoint; the other may be to successfully accomplish the virtual task; for example, the block or tackle.

In most game or test activities, there is a cooperative relationship/interaction between the "effectors", for example, the hand, and the involved joints, i.e. the hip, knee, wrist, elbow, shoulder(s). To be determined is the performance of the involved joints; for example, did the involved shoulder "lock down", etc.? In other applications there may be a cooperative relationship between the arms and shoulders. Or a cooperative relationship between the knee(s) as effectors and the subject's hips, etc.

Performance data relating to the movement of the effectors, i.e. the hands, may include, by way of example: were the hand(s) successful at "reaching" their intended "target"? Did they decelerate sufficiently to accomplish the task? Were the joints sufficiently aligned/oriented so as to be compliant with the principles of the Deceleration Constellation, etcetera? Did the spine exhibit proper verticality?

Muscles associated with the shoulders contribute to stabilizing/braking of the "punching" hand; and thereby enhancing deceleration capabilities. Specifically, the actions of the antagonistic shoulder muscles may assist in the deceleration/braking/"anchoring" of the involved hands. It may be material that the shoulder joint maintain in the same plane as the chest.

Was there shoulder movement in the same vector direction as the preceding fist? If so, what vector direction and magnitude? And if so, did said shoulder move consistent with the subject's Deceleration Constellation? Did it lock down at termination?

The relationship of the points defined by the Deceleration Constellation makes possible the characterization of the subject's posture/form to identify the intended technique, for example a punch, block, etc., and to critique its effectiveness.

Identifying Key Movement Patterns.

To be distinguished is shoulder movement "following" the punch, or any such movement due to the rotation of the entire Deceleration Constellation, with the shoulder remaining locked/fixed relative to the rest of the Constellation points.

Did the spine remain vertical during said aforementioned movement? Did the spine move over the subject's hips/legs? Was the lower extremity maintained in a stable posture with the torso positioned vertically over the legs?

As stated above, the moment to moment position (performance) of each hand, as well as the "shape" of each hand, may be tracked if determined material to the technique being taught.

Maintenance of proper body alignment ("verticality") may also be fundamental to the ability to effectively "fire"/contract the muscles responsible for protecting the involved joints (joint stabilization). As discussed herein, there is an increased risk of knee injury when the upper extremity fails to maintain verticality in relationship to the lower extremity.

Representative examples of training and assessment of complex techniques enabled by this invention may include, not are not limited to, a boxing punch, a two-hand palm strike as may be executed by a defensive football lineman, or a football tackle, throwing or catching a ball, moving a virtual object from place to place, etcetera. In each of these cases, the points comprising the player's Deceleration Constellation may be so aligned as to create an identifiable action.

Note that the subject may employ an implement such as a tennis racket or similar without, in many cases, deviating from the principles taught herein.

EMBODIMENTS

The TRAZER simulator or similar device provides means (SEE U.S. Pat. No. 9,078,598, issued Jul. 14, 2015) to track the subject's whole body positional changes in free space, as well as the absolute and relative positional changes of key body segments. TRAZER is one embodiment that may be used in this invention. TRAZER concurrently displays visual cues on a large screen that prompt the desired subject movements/responses.

TRAZER software could be written to include tracking the body points comprising the Deceleration Constellation to assess joint stabilization, as well as fundamental performance metrics and full body kinematics.

In its current configuration, TRAZER uses the Kinect sensor, with its 30 Hz frame rate. This tracking means may be insufficient to capture (track/measure) the deceleration and acceleration values prerequisite to the characterization of the subject's limb and body movements as taught herein. "Joint displacements", for example, of the shoulders may also be "invisible" to such cameras, which may negatively impact enablement of the current invention, depending on the game technique being trained, etc.

That said, the next generation TRAZER-type tracking devices may employ the just released Intel RealSense 400 camera series or equivalent, whose performance specs include a frame rate of up to 90 fps and a FOV of 91×65×100 degrees. This transition is currently underway.

Improved Tracking Via Body Worn Markers

Lightweight flexible "markers" may be worn on the subject's body at strategic locations to improve both the visibility and reliability of the present invention's tracking capabilities. By way of example, such markers could be made of reflective material and/or a suitably recognizable patterned material. They could be applied to the subject's clothing or woven into articles of clothing.

The use of commercially available 6-9 Degrees Of Freedom (DOF) sensors designed specifically for use in sports/athletics etc. is a viable option; either in combination with TRAZER-like sensing means or solo. Such sensors are available from companies such as: XSENS.com, APDM.com, SHIMMERSENSING.com, NOTCH.com and others.

Low cost body worn sensors may capture discreet body movements, i.e. the Deceleration Constellation, at relatively high frequencies/rates. That said, the measurement of absolute position might be more challenging.

Example mounting means may include an adjustable chest strap that may secure one or more discrete sensors strategically located in proximity of each "shoulder blade" (upper back) of the user. One purpose of such a mounting position is to observe/assess the degree of joint stabilization of the shoulder.

Mounting locations of interest whether for physically active or in-active populations, relating to the measurement/assessment of both joint stabilization and power generation, may include the wrists/hands, elbows, shoulders, hips, knees and ankles.

VR Headgear Delivering Visual Cues

The use of VR headgear coupled to, and in communication with, strategically positioned body worn sensors or other tracking means, may provide a compelling training and testing experience. One benefit of this configuration is its ability to present visual challenges in nearly all vector directions. The VR headgear acts to deliver the visual cues prompting the desired movements from the player.

The VR headgear would serve as the delivery system for providing graphical challenges to the subject, however, a second technology would be required to track and record the subject's movement in free space. Body worn sensors, as mentioned above, may incorporate the means for transmitting the desired data remotely, either to a sideline located receiving device, or, for example, to an iPad or laptop computer or to a body worn receiver, which, in any case, may communicate with the VR headgear.

Augmented Reality

Devices such as HoloLens purport to offer gaming activities that are overlaid onto the subject's view of the natural/real world, unlike virtual reality, which requires that the subject enter a world apart from the space he is moving in. This technology may provide a safe means of interfacing with virtual opponents and/or objects, however, as with VR headgear, a secondary means of tracking the subject's response to cues and gathering of movement data must be employed. This could be via body worn sensors or camera(s), for example.

Discerning Both Hand Position and Hand Shape.

The "shape" of the subject's hands may be material to compliance with the game challenge and/or task specific training and assessments. For example, the desired "shape" may be a fist in a punching game, an exposed palm in the role of a football defensive lineman, a "grab" in wrestling and so on. The hand shape assumed may be one that is deemed effective in satisfying the present activity/task, or in answering the question, "Was the technique correctly executed because the hands were in the proper shape?" Examples of hand specific training and assessments include football blocking and tackling, boxing, throwing/returning a ball, etc.

The body-worn markers described above could improve recognition of the "shape" of the subject's hand visible to the tracking camera. For example, to ascertain whether the hand was presented as a palm or fist. Essentially, a glove sans figures could be worn, made of a suitably reflective material, or a recognizable pattern or print in order to distinguish the palm from the top of the hand, for example. Full enablement of the present invention would benefit from means for identification of the subject's hand shape.

That said, capabilities limited to discern positional changes due to a singular point tracking method would satisfy questions such as: "Did the hand "reach" its intended "target"?" "Was its travel path efficient; its acceleration and subsequent deceleration metrics sufficient to accomplish the requisite task?" This limited approach is employed with the Kinect-based games; an approach that obviously fails to identify the "shape" of the subject's hands.

Calibration Means.

Regardless of the type of sensor(s) employed, calibration of the subject in order to mark the location of the involved joints prior to the initiation of his session may be an important step.

The inter-relationship of the location of the shoulders when at rest with the top of the spine, for example, or the hips in relationship to the base of the spine, may contribute information key to determining the quality of execution of the technique.

One means of "calibration" is instructing the subject to assume and maintain the "correct" (desired) posture throughout the entire execution of the desired technique, such as a tackle or block in slow motion or full speed. In this way, the TRAZER or other tracking means would proceed to "personalize" the subject's action on a "frame by frame" basis with accommodations for differences in subject's technique, body dimensions, etcetera.

What is claimed is:

1. A method of conducting a neuromechanical assessment on a subject, said method comprising:
   prompting the subject to engage in a simulation of a reaction-based activity;
   wherein during said reaction-based activity, directing the subject to engage in locking down, wherein locking down includes a synergistic contraction of a muscle group and a forceful deceleration at a completion of a technique:
   tracking movement of the subject while the subject is engaged in said simulation;
   gathering data representing a whole body positional movement of the subject that includes an array of anatomical points of the subject wherein said data includes a deceleration constellation of the subject engaged in said simulation wherein said deceleration constellation is a spatial and a temporal relationship between said array of anatomical points;
   evaluating said data including at least said spatial relationship between two or more points of said array of anatomical points obtained in said gathering step; and
   displaying on a screen a visual representation of the subject engaged in said simulation of the reaction-based activity.

2. The method of claim 1 wherein said neuromechanical assessment includes a concussion assessment of the subject.

3. The method of claim 1 wherein said gathering step includes gathering data that represents a magnitude and timing of accelerations and decelerations of said array of anatomical points of the subject; and
   further comprising comparing said accelerations and decelerations of said array of anatomical points of the subject with a baseline assessment or an ideal template, said baseline assessment includes data representative of a previously gathered profile of the subject and said ideal template includes data representative of a proper reaction-based activity.

4. The method of claim 3 wherein said baseline assessment of the subject includes values representing braking and propulsion forces; and
   further comprising at least one of comparing a reaction time of said subject with said baseline assessment, and comparing a reaction acceleration with said baseline assessment.

5. The method of claim 1 wherein said array of anatomical points are representative of at least one effector of the subject.

6. The method of claim 5, wherein said gathering step includes data representing an upper body movement and a lower body movement of said subject during said simulation;
   wherein said evaluating step includes identifying at least one movement signature performed by the subject; and
   further comprising comparing said at least one movement signature performed by the subject with a baseline assessment or an ideal template.

7. The method of claim 5 wherein said evaluating step includes identifying a difference from a movement signature performed by the subject to identify a heightened risk of injury or an existing performance deficit wherein said movement signature is a defined reaction-based movement of the subject including at least one of a step, walk, run, tackle, block, kick, strike, hit, punch, push, pull, swing, catch, jump, lunge, squat, and throw.

8. A method of improving at least one of joint stabilization and reaction-based performance, said method comprising;
   directing a subject to engage in a reaction-based movement such that the subject is directed to respond via locking down wherein locking down includes a synergistic contraction of a muscle group and a forceful deceleration at a completion of a technique:
   tracking movement of the subject while the subject is engaged in said reaction-based movement;
   gathering data that represents the movement of an array of anatomical points of the subject wherein said data represents a deceleration constellation of the subject engaged in said reaction-based movement wherein said deceleration constellation is a spatial and a temporal relationship between said array of anatomical points;
   evaluating data including at least said spatial relationship between two or more points of said array of anatomical points obtained in said gathering step; and
   displaying on a screen a visual representation of the subject engaged in reaction-based movement.

9. The method of claim 8 wherein said directing step includes prompting the subject to engage in whole body movement and the gathering step includes gathering data that represents a whole body positional movement of the subject.

10. The method of claim 9, wherein during said gathering step, data that identifies whole body movement is gathered and during the evaluation step the data representing whole body movement is evaluated to determine if an upper body of the subject includes a proper spine alignment of the subject or to determine if a lower body of the subject includes a proper alignment of a knee position.

11. The method of claim 9, wherein said directing step includes prompting the subject to move to a position to catch a virtual ball.

12. The method of claim 11, wherein said evaluating step includes determining if the subject has demonstrated a kinematic form and a joint stabilization of the subject at the moment of catching said virtual ball to determine a catch or a drop of said virtual ball.

13. The method of claim 8 wherein said array of anatomical points of the subject represent at least one effector of the subject and the gathering step includes gathering data that represents spatial, temporal, accelerations, and decelerations of the array of anatomical points of the subject engaged in said reaction-based movement; and further comprising comparing accelerations and decelerations of at least one effector of the subject as the subject is engaged in a reaction-based movement to accelerations and decelerations of an effector of a subject in a baseline assessment.

14. The method of claim 13 wherein said locking down is concurrent with correct full body posture and/or correct technique.

15. The method of claim 8 wherein said array of anatomical points are representative of at least one effector of the subject.

16. The method of claim 15, further comprising detecting an altered gait termination status of said subject in a concussion assessment wherein said altered gait termination status is detected by comparing braking and propulsion forces of said subject engaged in a reaction-based movement with braking and propulsion forces of a baseline assessment.

17. The method of claim 8, wherein said evaluating step includes identifying a difference from said movement signature performed by the subject to identify a heightened risk of injury or an existing performance deficit wherein said movement signature is a defined reaction-based movement of the subject including at least one of step, walk, run, tackle, block, kick, strike, hit, punch, push, pull, swing, catch, jump, lunge, squat, and throw.

18. The method of claim 8 wherein said an array of anatomical points are representative of an involved joint of the subject, the involved joint includes at least one of a shoulder, elbow, wrist, knee, ankle, and hip.

19. The method of claim 8 further comprising calibrating a spatial relationship of said array of anatomical points of said subject prior to directing said subject to engage in said reaction-based movement.

* * * * *